(12) United States Patent
Piestrup et al.

(10) Patent No.: US 10,870,020 B2
(45) Date of Patent: Dec. 22, 2020

(54) NEUTRON SOURCE FOR NEUTRON CAPTURE THERAPY

(71) Applicant: Adelphi Technology, Inc., Redwood City, CA (US)

(72) Inventors: Melvin Arthur Piestrup, Redwood City, CA (US); Craig Mathew Brown, Santa Clara, CA (US); Allan Xi Chen, Daly City, CA (US); Charles Kevin Gary, Palo Alto, CA (US); Yao Zong Guan, San Francisco, CA (US); Yoshio Horii, Fukushima (JP); Glenn Emerson Jones, Jr., Pittsburg, CA (US); Yuji Kokubo, Fukushima (JP); Naoyuki Yamada, Fukushima (JP); Shotaro Komura, Fukushima (JP)

(73) Assignee: Adelphi Technology, Inc., Redwood City, CA (US)

(*) Notice: Subject to any disclaimer, the term of this patent is extended or adjusted under 35 U.S.C. 154(b) by 0 days.

(21) Appl. No.: 16/905,342

(22) Filed: Jun. 18, 2020

(65) Prior Publication Data

US 2020/0324145 A1 Oct. 15, 2020

Related U.S. Application Data

(60) Division of application No. 16/662,523, filed on Oct. 24, 2019, now Pat. No. 10,737,121, which is a continuation-in-part of application No. 15/488,983, filed on Apr. 17, 2017, now Pat. No. 10,603,516, which is a continuation of application No. 14/190,389, filed on Feb. 26, 2014, now Pat. No. 9,636,524, which is a continuation of application No. 13/532,447, filed on Jun. 25, 2012, now abandoned.

(60) Provisional application No. 61/571,406, filed on Jun. 27, 2011, provisional application No. 62/749,875, filed on Oct. 24, 2018.

(51) Int. Cl.
*G21G 1/06* (2006.01)
*A61N 5/10* (2006.01)
*G21G 4/02* (2006.01)

(52) U.S. Cl.
CPC .......... *A61N 5/1077* (2013.01); *A61N 5/10* (2013.01); *G21G 4/02* (2013.01); *A61N 2005/109* (2013.01); *A61N 2005/1094* (2013.01); *A61N 2005/1095* (2013.01)

(58) Field of Classification Search
CPC .................... A61N 5/1077; G21G 4/02
See application file for complete search history.

(56) References Cited

U.S. PATENT DOCUMENTS

| | | | |
|---|---|---|---|
| 5,433,693 A * | 7/1995 | Ott | A61N 5/10 600/1 |
| 2010/0061500 A1* | 3/2010 | Lou | G21G 4/02 376/114 |

* cited by examiner

*Primary Examiner* — Marshall P O'Connor
(74) *Attorney, Agent, or Firm* — Donald R. Boys; Central Coast Patent Agency LLC

(57) ABSTRACT

A Boron neutron cancer treatment system has a secondary moderator having a central treatment chamber for a subject, and eight substantially identical neutron generators, each comprising a pre-moderator block. The eight neutron generators are positioned around the secondary moderator with the axis of each acceleration chamber passing through the center of the treatment chamber, and with the angled sides of the neutron generators fully adjacent.

6 Claims, 26 Drawing Sheets

NEUTRON SOURCE FOR NEUTRON CAPTURE THERAPY

CROSS REFERENCED TO RELATED APPLICATIONS

This present application is a divisional application of co-pending U.S. application Ser. No. 16/662,523, filed 24 Oct. 2019, which claims priority to provisional application 62/749,875, filed Oct. 24, 2018, and which is a continuation in part (CIP) of U.S. application Ser. No. 15/488,983, filed Apr. 17, 2017, which claimed priority to U.S. application Ser. No. 14/190,389, filed Feb. 26, 2014, which has issued as U.S. Pat. No. 9,636,524 on May 2, 2017, which claimed priority to U.S. application Ser. No. 13/532,447, filed on Jun. 25, 2012, now abandoned, which claimed priority to provisional U.S. patent application 61/571,406 filed Jun. 27, 2011.

BACKGROUND OF THE INVENTION

1. Field of the Invention

This invention is in the technical area of apparatus and methods for Boron Neutron capture therapy for cancer.

2. Description of Related Art

Boron Neutron Capture Therapy (BNCT) is not new in the art, as thermal neutrons have been used for cancer therapy for the destruction of cancer tumors. These neutrons interact with boron-10 that has been placed at the cancer site. The neutrons interact with the boron to produce fission events whereby alpha particles and lithium nuclei are created. These massive ionized particles are then released, destroying the chemical bonds of nearby cancer tumor cells. At present the neutrons created in a reactor or accelerator pass through a moderator, which shapes the neutron energy spectrum suitable for BNCT treatment. While passing through the moderator and then the tissue of the patient, the neutrons are slowed by collisions and become low energy thermal neutrons. The thermal neutrons undergo reactions with the boron-10 nuclei at a cancer site, forming compound nuclei (excited boron-11), which then promptly disintegrate to lithium-7 and an alpha particle. Both the alpha particle and the lithium ion produce closely spaced ionizations in the immediate vicinity of the reaction, with a range of approximately 5-9 micrometers, or roughly the thickness of one cell diameter. The release of this energy destroys surrounding cancer cells. This technique is advantageous since the radiation damage occurs over a short range and thus normal tissues can be spared.

Gadolinium can also be considered as a capture agent in neutron capture therapy (NCT) because of its very high neutron capture cross section. A number of gadolinium compounds have been used routinely as contrast agents for imaging brain tumors. The tumors have absorbed a large fraction of the gadolinium, making gadolinium an excellent capture agent for NCT. Therefore, GNTC may also be considered as a variation in embodiments of the present invention.

The following definitions of neutron energy ranges, E, are used frequently by those skilled in the art of producing and using neutrons for medical, commercial and scientific applications: Fast (E>1 MeV), Epithermal (0.5 eV<E<1Mev) and Thermal (E<0.5 eV) neutrons.

BNCT has the potential to treat previously untreatable cancers such as glioblastoma multiforme (GBM). In the US brain tumors are the second most frequent cause of cancer-related deaths for males under 29 and females under 20. GBM is nearly always fatal and has, until now, no known effective treatment. There are approximately 13,000 deaths per year due to primary brain tumors.

If conventional medicine is used where the glioblast is excised, new tumors almost invariably recur, frequently far from the original tumor site. Effective radiation therapy, therefore, must encompass a large volume and the radiation must be uniformly distributed. Conventional radiation treatment is usually too toxic to be of use against GBM.

For distributed tumors, effective radiation therapy must encompass a larger volume and the radiation must be uniformly distributed. This is also true of liver cancers. The liver is the most common target of metastases from many primary tumors. Primary and metastatic liver cancers are usually fatal, especially after resection of multiple individual tumors. The response rate for nonresectable hepatocellular carcinoma to traditional radiation treatment or chemotherapy is also very poor. However, recent results indicate that the thermal neutron irradiation of the whole liver with a $^{10}B$ compound, to be bombarded with low-energy neutrons, could be a way to destroy all the liver metastases.

Recent research in BNCT has shown that neutron capture therapy can be used to treat a large number of different cancers. BNCT has been found to be effective and safe in the treatment of inoperable, locally advanced head and neck carcinomas that recur at sites that were previously irradiated with traditional gamma radiation. Thus, BNCT could be considered for a wider range of cancers. BNCT holds such promise because the dose to the cancer site can be greatly enhanced over that produced by y-radiation sources. This is a consequence of the fact that the neutron-boron reaction produces the emission of short-range (5-9 um distance) radiation, and consequently normal tissues can be spared. In addition, boron can achieve a high tumor-to-brain concentration ratio, as much as ten or more, thereby preferentially destroying abnormal tissue.

BNCT has been tested using either nuclear reactors or accelerators to produce the neutrons, which are not practical or affordable for most clinical settings. Reactors also do not produce an ideal neutron spectrum and are contaminated with y-radiation.

Fusion generators produce fast neutrons from the deuterium-deuterium (DD) or the deuterium-tritium (DT) reactions and are, in general, smaller and less expensive than accelerators and reactors. Fast neutrons thus produced must be moderated or slowed down to thermal or epithermal neutron energies using, for example, water or other hydrogen bearing materials.

The fusion neutron generator has three basic components: an ion source, an electron shield and an acceleration structure with a target. The ions are accelerated from the ion source to usually a titanium target using a high voltage potential of between 40 kV to 200 kV, which can be easily delivered by a modern high voltage power supply. An electron shield is usually disposed between the ion source and the titanium target. This shield is voltage biased to repel electrons being generated when the positive D+ ions that strike the titanium target. This prevents these electrons from striking the ion source and damaging it due to electron heating.

The target uses a deuterium $D^+$ or tritium $T^+$ absorbing material such as titanium, which readily absorbs the $D^+$ or $T^+$ ions, forming a titanium hydride. Succeeding $D^+$ or $T^+$ ions strike these embedded ions and fuse, resulting in DD, DT or TT reactions and releasing fast neutrons.

Prior attempts at proposing fusion generators required the use of the DT reaction with the need for radioactive tritium and high acceleration powers. High yields of fast neutrons/sec were needed to achieve enough thermal neutrons for therapy in a reasonable length of time of therapy treatments. These prior schemes for achieving epithermal neutron fluxes are serial or planar in design: a single fast neutron generator is followed by a moderator, which is followed by the patient. Unfortunately, since the neutrons are entering from one side of the head, the planar neutron irradiation system leads to a high surface or skin dosage and a decreasing neutron dose deeper into the brain. The brain is not irradiated uniformly, and cancer sites have lower thermal neutron dosage the further they are from the planar port.

A conventional planar neutron irradiation system 14 and its operation is shown in FIG. 1 labeled Prior Art. Conversion of fast neutrons 22 to thermal neutrons 30 takes place in a series of steps. First the fast neutrons 22 are produced by a cylindrical fast neutron generator 20 and then enter a moderating means 18 where they suffer elastic scatterings (collisions with nuclei of the moderating material's atoms). This lowers the fast neutrons to epithermal neutron 24 energies. A mixture of epithermals 24 and thermal neutrons 30 are emitted out of a planar port 16 and then enter the patient's head 26. The epithermal neutrons 24 are moderated still further in the patient's brain and moderated further to thermal neutrons, finally being captured by the boron at the tumor site. The fission reaction occurs, and alpha and Li-7 ions are released, destroying the tumor cells.

The epithermal and thermal neutrons reach the patient's head through a planar port 16 formed from neutron absorbing materials that form a collimating means 28. The thermal and epithermal neutrons strike the patient's head on one side, and many neutrons escape or are not used. One escaping neutron 38 is shown as representative. This is an inefficient process requiring a large number of fast neutrons to be produced in order to produce enough thermal neutrons for reasonable therapy or treatment times (e.g. 30 min). To achieve higher yields of fast neutrons the planar neutron irradiation system 14 requires that one use either the DD fusion reaction with extremely high acceleration powers (e.g. 0.5 to 1.5 Megawatts) or the DT reaction which has an approximate 100-fold increase in neutron yield for the same acceleration power.

The use of tritium has a whole host of safety and maintenance problems. Tritium gas is radioactive and extremely difficult to eliminate once it gets on to a surface. In the art of producing fast neutrons this requires that the generator be sealed and have a means for achieving a vacuum that is completely sealed. The generator head cannot be easily maintained and usually its lifetime is limited to less than 2000 hours. This reduces the possible use of this generator for clinical operation since the number of patients who could be treated would be small before the generator head would need replacement.

On the other hand, the use of the DD fusion reaction allows one skilled in the art to use an actively-pumped-vacuum means with roughing and turbo pumps. The generator can then be opened for repairs and its lifetime extended. This makes the DD fusion reaction neutron generator optimum for clinical use. The downside for the DD fusion reaction is that high acceleration powers are required to achieve the desired neutron yield required by prior art methods. Improving the efficiency of producing the right thermal neutron flux at the cancer site is imperative for achieving BNCT in a clinical and hospital setting.

SUMMARY OF THE INVENTION

In one embodiment of the invention a Boron neutron cancer treatment system is provided, comprising a secondary moderator having a central treatment chamber for a subject, and eight substantially identical neutron generators, each comprising a pre-moderator block of moderating material having an upper surface, a lower surface, a first and a second end, opposite side surfaces angled inward by forty-five degrees along at least a portion of the height, a first length, a first width substantially less than the first length, and a first thickness, a cylindrical acceleration chamber having a first diameter substantially the first width of the pre-moderator block, sealed at one end to the upper surface of the pre-moderator block adjacent the first end of the pre-moderator block, with a vertical axis perpendicular to the upper surface, the acceleration chamber having a height and a top cover at a second end away from the pre-moderator block, a vacuum pump engaging the acceleration chamber at a right angle to the vertical axis, evacuating the acceleration chamber to a moderately high vacuum, a plasma ion chamber opening into the acceleration chamber through an ion extraction iris through the top cover of the acceleration chamber on the vertical axis of the acceleration chamber, a gas source providing deuterium gas to the plasma ion chamber, a microwave energy source ionizing the gas in the plasma ion chamber, a cylindrical primary isolation well extending a substantial distance into the pre-moderator block from the upper surface, centered on the vertical axis of the acceleration chamber, a secondary isolation well substantially in a shape of a hollow cylinder surrounding the primary isolation well, to a depth somewhat less than the substantial distance of the primary isolation well, within the first diameter of the acceleration chamber, a water-cooled titanium target disk having a target surface orthogonal to the axis of the acceleration chamber, the target disk having a diameter substantially smaller then a diameter of the isolation well, positioned at a lower extremity of the isolation well, the target disk biased to a substantial negative DC voltage, and electrically grounded metal cladding covering all otherwise exposed surfaces of the pre-moderator block. The eight neutron generators are positioned around the secondary moderator with the axis of each acceleration chamber passing through the center of the treatment chamber, and with the angled sides of the neutron generators fully adjacent.

In one embodiment the system further comprises eight substantially rectangular spacing blocks of moderator material, one spacing block placed between each adjacent neutron generator with sides of the spacing blocks fully adjacent with the angled sides of the neutron generators. Also, in one embodiment the secondary moderator is shaped to fill all volume between the neutron generators and the central treatment chamber. Also, in one embodiment the secondary moderator is a block or blocks of solid moderator material. In one embodiment the secondary moderator is a container filled with heavy water. And in one embodiment the secondary moderator is a container filled with granulated moderator material.

BRIEF DESCRIPTION OF THE DRAWING FIGURES

Figure 12A:
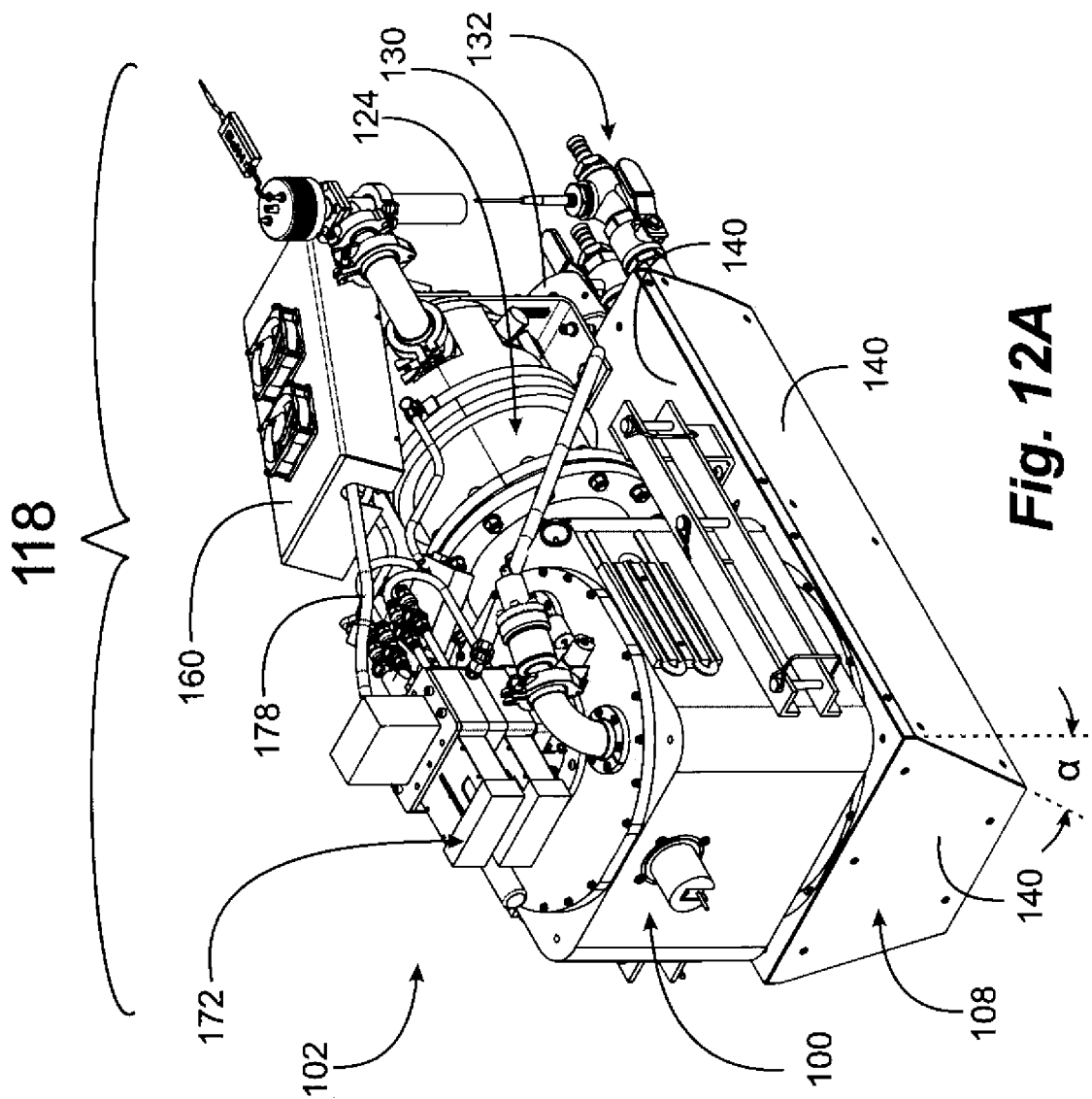
FIG. 12A is a perspective view of a modular neutron generator in an embodiment of the invention.

FIG. 12 B is a perspective cross-section view of the module of FIG. 12A taken along an axis of the acceleration chamber, at a right angle to an axis of the turbo vacuum pump.

FIG. 12 C is a perspective cross-section view of the module of FIG. 12A taken along an axis of the turbo vacuum pump.

FIG. 13 A is a planar view of six modular generators arrayed around a moderator and chamber for a patient, in an embodiment of the invention.

FIG. 13 B is a perspective view of the system of FIG. 13 using six modular neutron generators in an embodiment of the invention.

FIG. 13 C is a perspective view of a cylindrical neutron irradiation system using eight modular generators with one removed to show how an irradiation system is assembled in an embodiment of the invention.

FIG. 13 D is a planar diagram of modular generators with a fluid moderator and arrayed to maximize dose to a cancer site in a brain, in an embodiment of the invention.

FIG. 14 A is a simplified, mostly diagrammatical view of a central cylinder with a human head (phantom) inside a helmet moderator and neutron reflector with eight modular neutron generators in an embodiment of the invention.

Figure 14A:
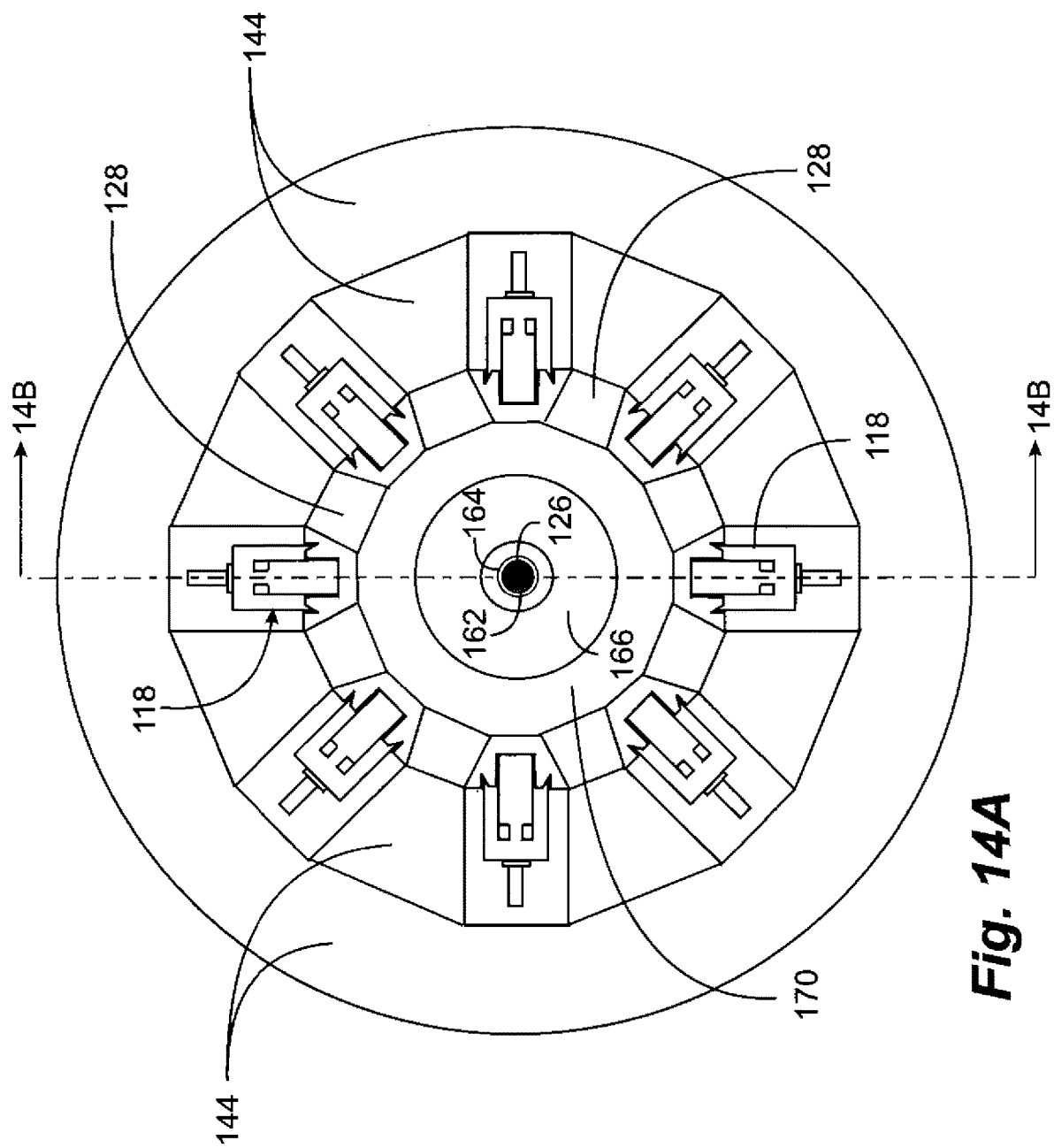
Figure 14B:
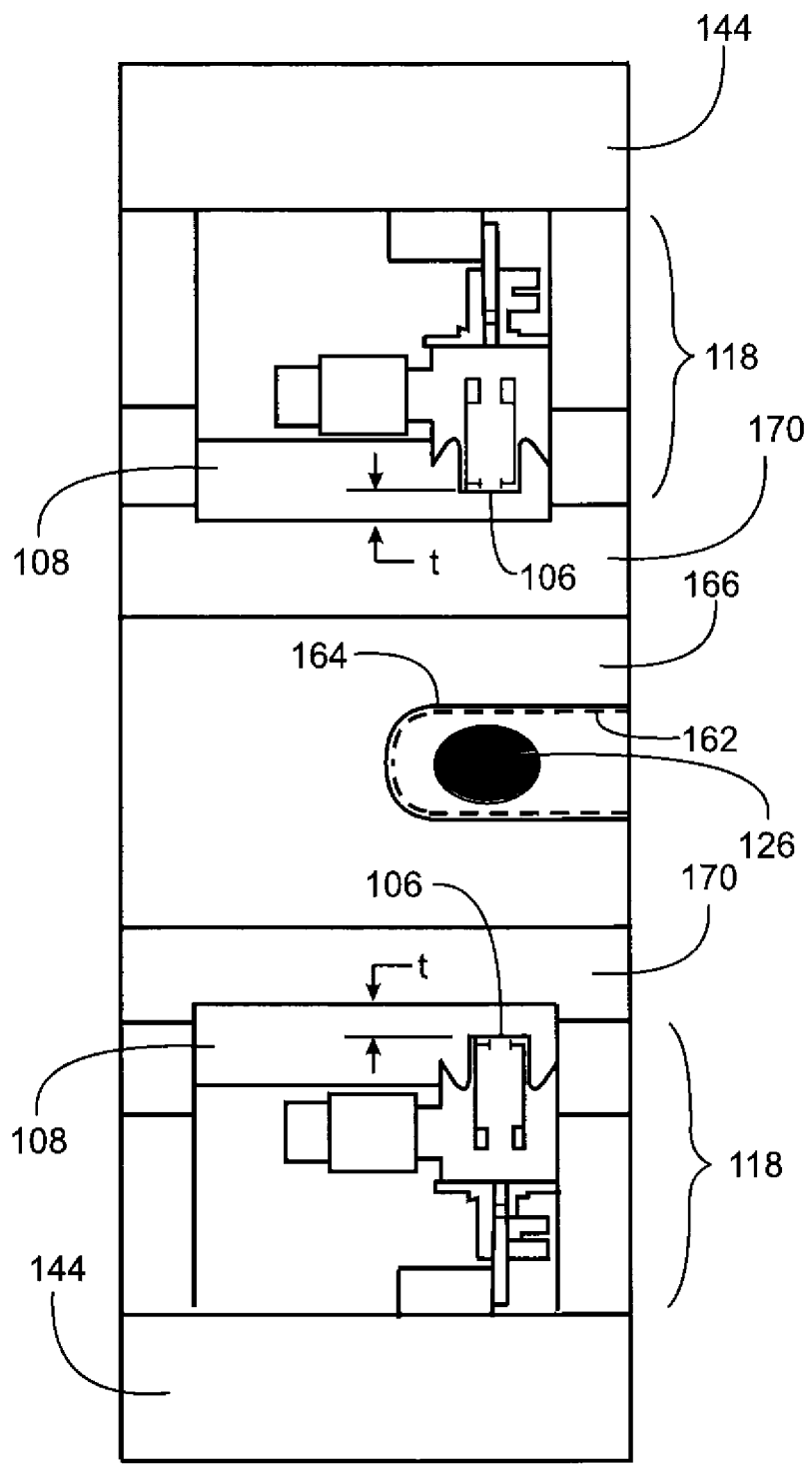

FIG. 14B is a simplified, mostly diagrammatical section view taken along section line 14B-14B of FIG. 14A.

Figure 15:
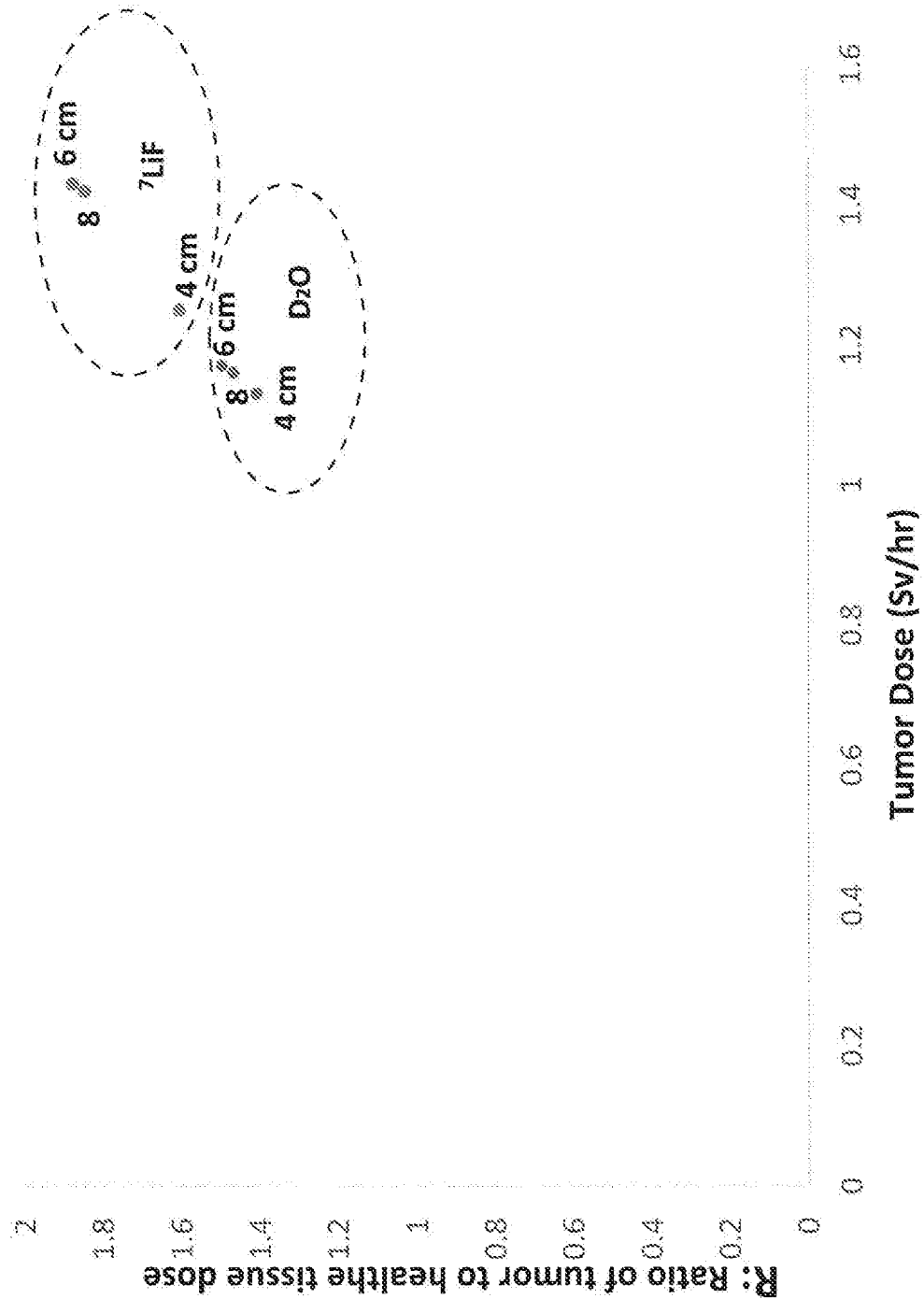

FIG. 15 is a graph showing an expected horizontal dose equivalent rate (Sv/hr) as a function of horizontal position across a phantom (head) in an embodiment of the invention.

Figure 16A:
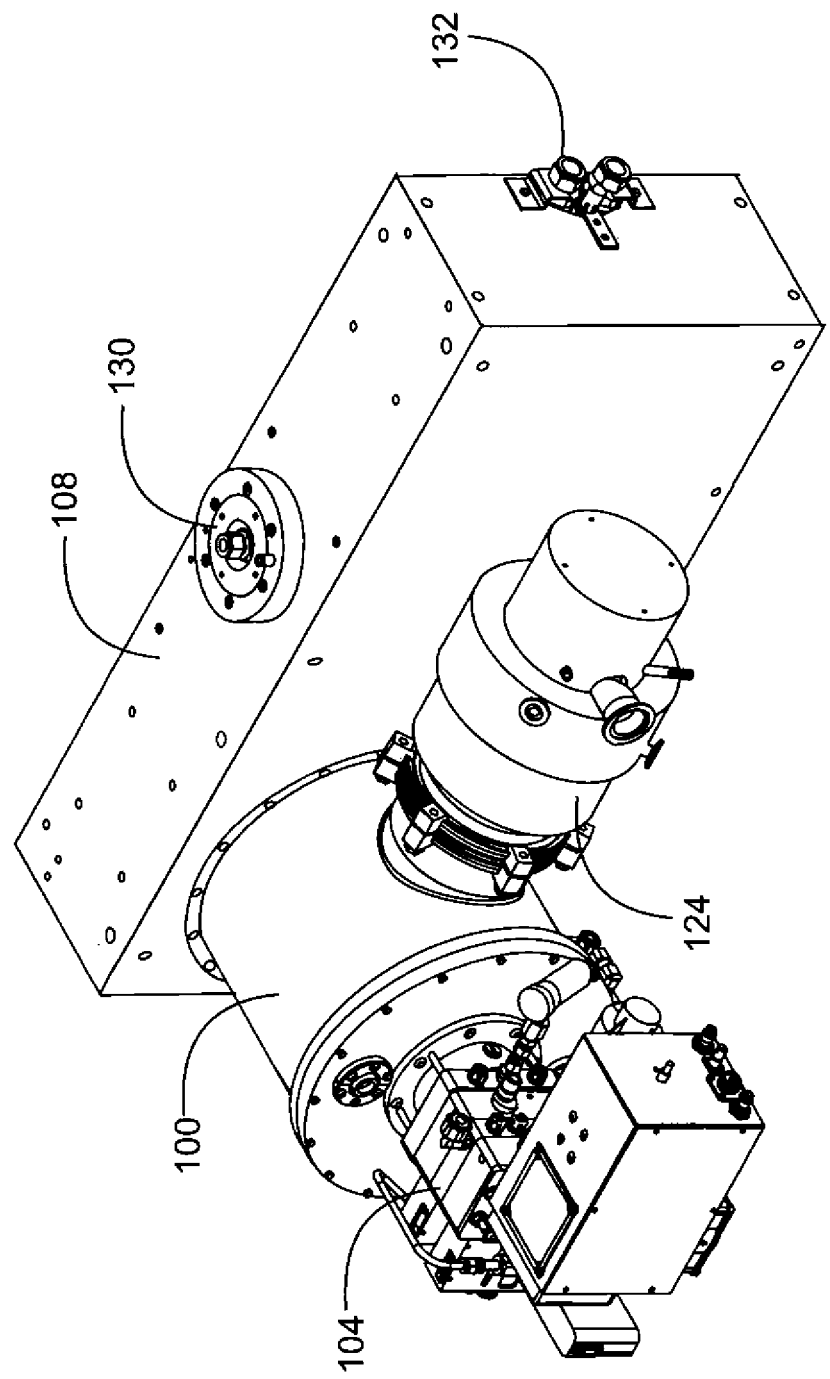

FIG. 16A is a perspective view of a module for a small animal neutron radiation system employing four modules.

Figure 16B:
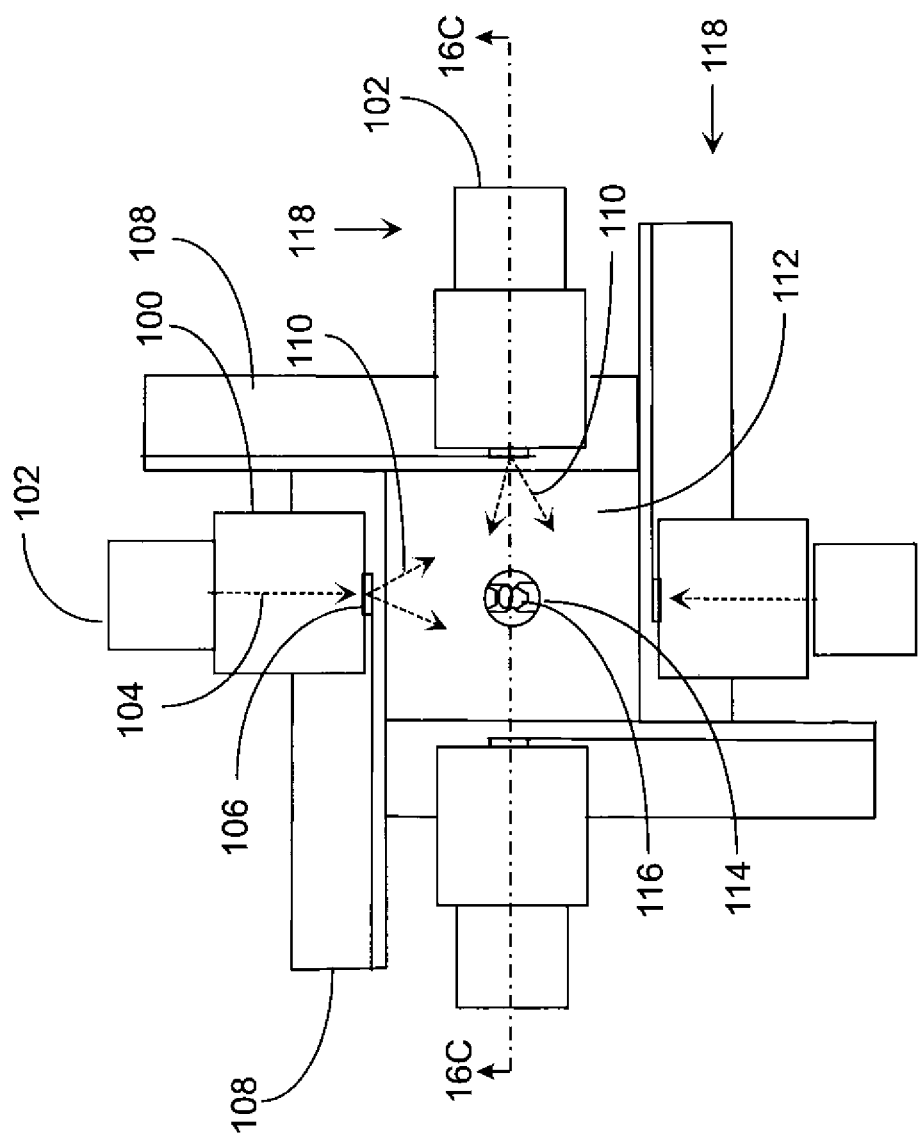

FIG. 16B is a simplified top plan view of the small animal neutron irradiation system of FIG. 16A.

Figure 16C:
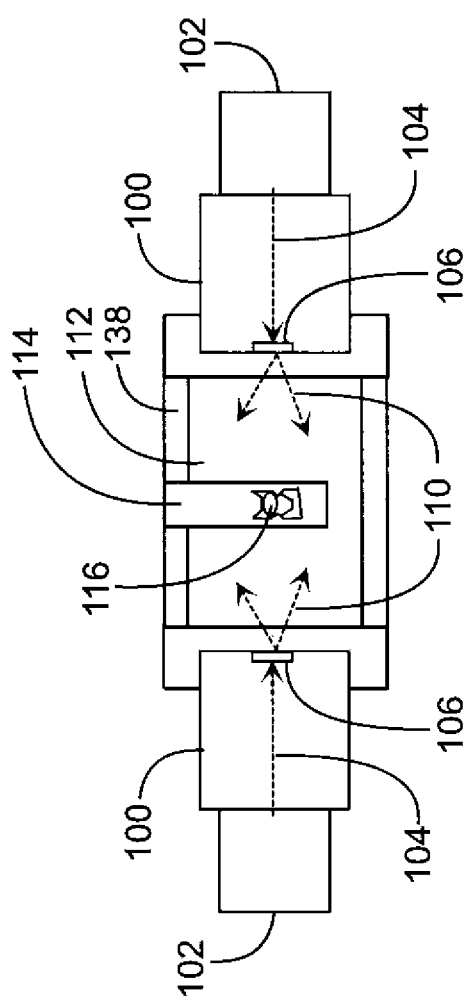

FIG. 16C is a simplified cross section of the small animal neutron irradiation system of FIG. 16A.

Figure 16D:
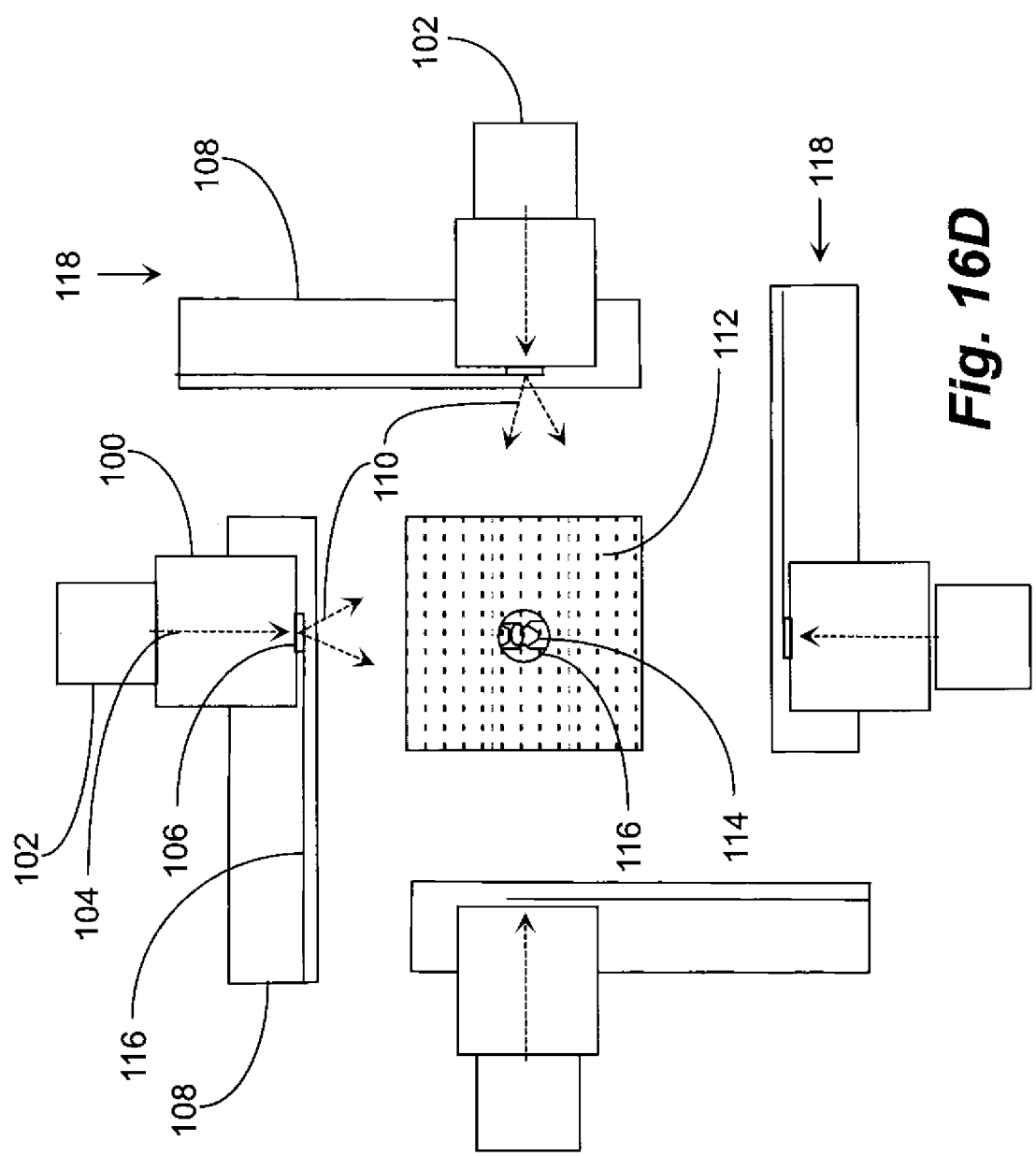

FIG. 16D is an exploded plan view of the small animal neutron irradiation system of FIG. 16A.

DETAILED DESCRIPTION

In the following descriptions reference is made to the accompanying drawings that form a part hereof, and in which are shown by way of illustration specific embodiments in which the invention may be practiced. It is to be understood that other embodiments may be utilized, and structural changes may be made without departing from the scope of the present invention.

Uniform Delivery of Thermal Neutrons to the Cancer Sites

To achieve extremely high thermal neutron fluxes uniformly distributed across a patient's head, for example, a hemispherical geometry is used in one embodiment of the invention. This unique geometry arranges fast neutron sources in a circle around a moderator whose radial thickness is optimized to deliver a maximum thermal neutron flux to a patient's brain. This embodiment produces a uniform thermal neutron dose within a factor of $\frac{1}{20}^{th}$ of the required fast neutron yield and line-voltage input power of a conventional planar neutron irradiation system. This arrangement permits using a relatively safe deuterium-deuterium (DD) fusion reaction (no radioactive tritium) and commercial high voltage power supplies operating at modest powers (50 to 100 kW).

Figure 2:
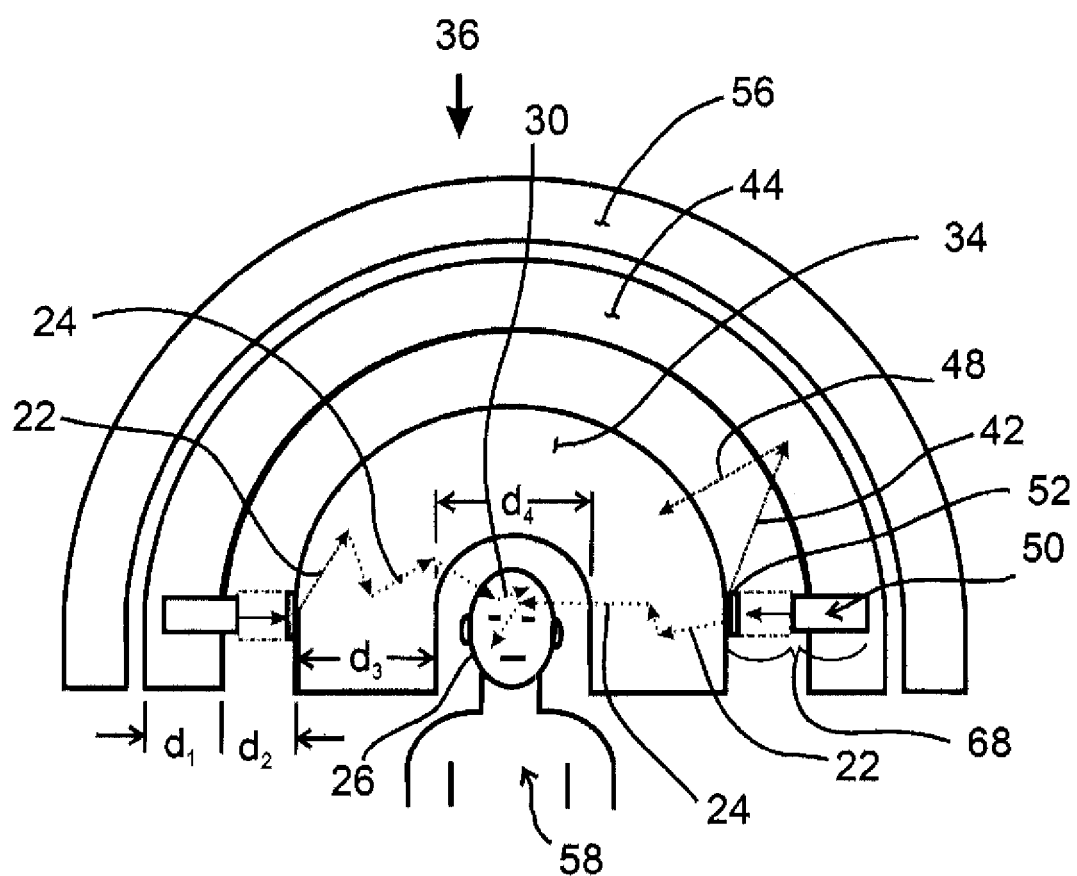
FIG. 2 is a cross sectional view of an embodiment of how multiple fast neutron generators are arranged around a hemispheric moderator to introduce a uniform thermal neutron dose into a patient's head.

FIG. 2 is a cross sectional view of a hemispheric neutron irradiation system 36 according to one embodiment of the invention. Multiple fast neutron generators 68 surround a hemispheric moderator 34, which in turn surrounds the patient's head 26. Titanium targets 52 are distributed around the perimeter of the hemispheric moderator 34. Surrounding the moderator 34 and the fast neutron generators 68 is a fast-neutron reflector 44.

In the moderator 34, moderating material such as $^7$LiF, high density polyethylene (HDPE), and heavy water are shaped in a hemisphere that is shaped around the head of the patient. The optimum thickness of the hemispheric moderator for irradiation purposes is dependent upon the material's nuclear structure and density.

Figure 3:
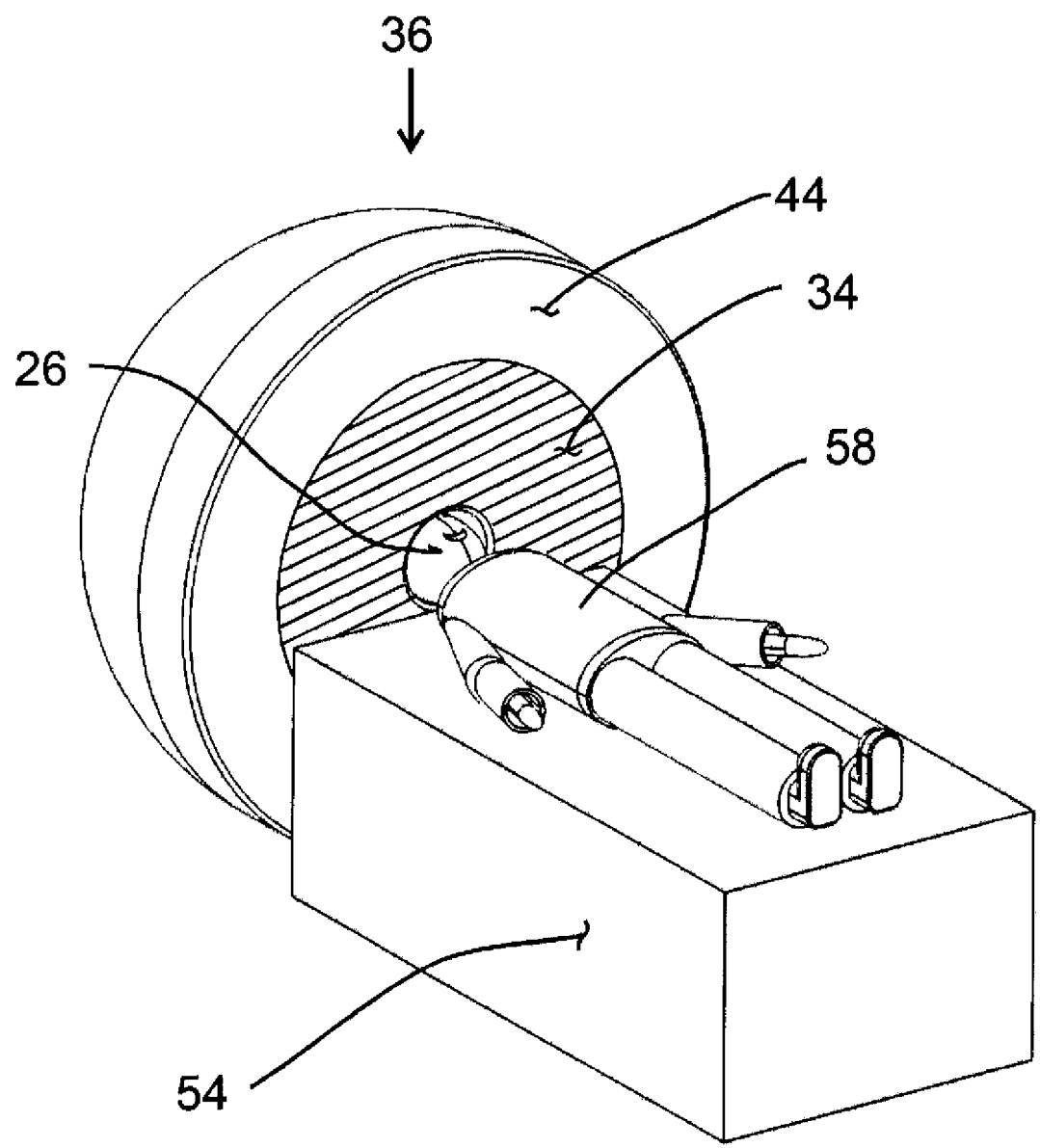
FIG. 3 is a perspective view of how multiple fast neutron generators are used in an embodiment of the invention to develop a high neutron dose into a patient's head.

FIG. 3 shows a perspective view of a patient 58 on a table 54 with the patient's head inserted into hemispheric irradiation system 36. The patient 58 lies on the table 54 with his head inserted into hemispheric moderator 34. Surrounding the moderator is neutron reflecting material 44, such as lead or bismuth.

Referring again to FIG. 2, fast neutrons 22 are produced by fast neutron generators 68. Generators 68 are composed of titanium targets 52 and ion sources 50. Ion beams are produced by ion sources 50 and accelerated toward titanium targets 52 which are embedded in hemispheric moderator 34. A DD fusion reaction occurs at the target, producing 2.5 MeV fast neutrons 22.

The fast neutrons 22 enter the moderator 34 wherein they are elastically scattered by collisions with the moderator atom's nuclei. This slows them down after a few collisions to epithermal neutrons 24 energies. These epithermal neutrons 24 enter the patient's head 26 wherein they are moderated further to thermal neutron 30 energies. These thermal neutrons 30 are then captured by boron-10 nuclei at the cancer site, resulting in a fusion event and the death of proximal cancer cells.

Fast neutrons 22 are emitted isotropically from titanium target 52 in all directions. Outwardly traveling fast neutrons 42 are reflected back (reflected neutron 48) by fast neutron reflector 44, while inwardly traveling fast neutrons 40 are moderated to epithermal energies and enter the patient's head 26, where further moderation of the neutrons to thermal energies occurs.

A shell of protective shielding 56 is also shown in FIG. 2. In some embodiments, this may be necessary for shielding both the patient and the operator from excessive irradiation due to neutrons, x-rays and gamma radiation. The shielding can be made of a variety of materials depending upon the radiation components one wishes to suppress.

In some embodiments, fast neutron reflector 44 is made of lead or bismuth. The fast neutron reflector also acts as a shielding means to reduce emitted gamma rays and neutrons from the hemispherical neutron irradiation system 36. As one skilled in the art will realize, gamma-absorbing or other neutron reflector means can be placed in layers around the hemispherical neutron irradiation system 36 to reduce spurious and dangerous radiation from reaching the patient 58 and the operator.

Hemispheric moderator 34, fast neutron reflector 44 and head 26 act together to concentrate the thermal neutrons in the patient's head. The patient's head and the moderator 34 act in concert as a single moderator. With a careful selection of moderating materials and geometry, a uniform dose of thermal neutrons can be achieved across the patient's head and, if a boron drug is administered, a large and uniform therapeutic ratio can be achieved.

The invention gives a uniform dose of thermal neutrons to the head while minimizing the fast neutron and gamma contributions. The required quantity of fast neutrons to initiate this performance is reduced compared to that of prior art planar neutron irradiation systems (see FIG. 1).

Figure 4:
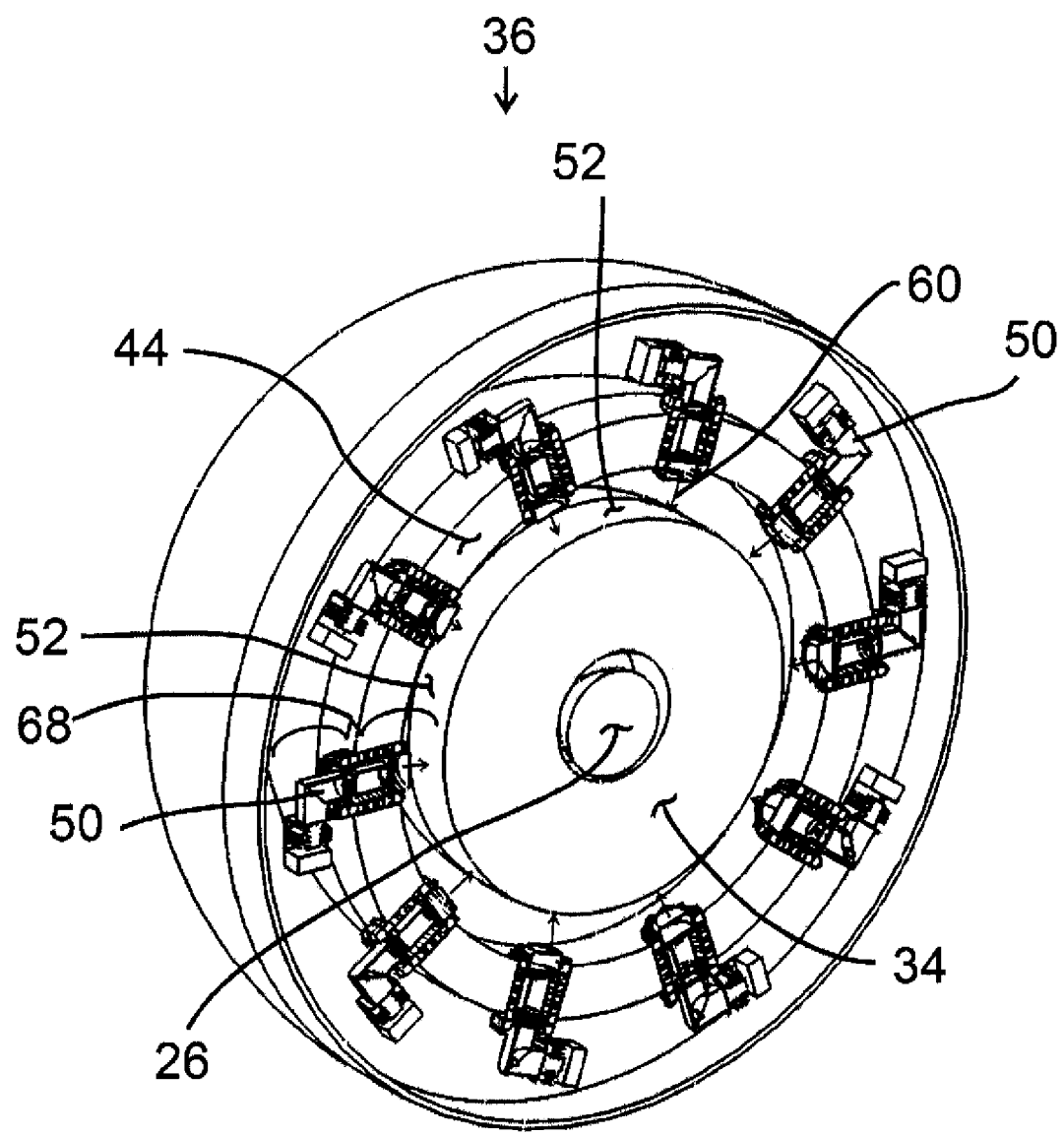
FIG. 4 is a cross sectional view of the arrangement of FIG. 3 with the patient's head inside the interior of the neutron irradiation system.

A cross section perspective view of the hemispheric neutron irradiation system 36 in an embodiment of the invention is shown in FIG. 4. This cross-section view is of a radial cut directly through the patient's head 26 and hemispherical neutron irradiation system 36. As shown in this embodiment, ten fast-neutron generators 68 composed of ion sources 50 with titanium targets 52 are radially surrounding the hemispheric moderator 34 and the patient's head 26. The titanium target 52 in this embodiment is a continuous belt of titanium surrounding the moderator 34. The titanium targets can also be segmented, as was shown in FIG. 2. The ion sources in this embodiment are embedded in fast neutron reflector 44.

There are a number of materials one could select for the moderator 34 to achieve maximum thermal neutron flux at the patient's head 26. The performance of HDPE, heavy water ($D_2O$), graphite, $^7LiF$, and $AlF_3$ was analyzed using the Monte Carlo Neutral Particle (MCNP) simulation. In general, there is an optimum thickness for each moderator material that generates the maximum thermal flux at the patient's head (or other body part or organ). The thermal neutrons/($cm^2$-s) was calculated for these materials as a function of moderator thickness $d_3$, where $d_4$=25 cm, and fast neutron reflector 44 is $d_1$=50 cm thick and is made of lead. As in all our calculations, the combined fast neutron yield striking the area from all the fast neutron generators 68 is assumed in the MCNP to be $10^{11}$ n/s. The optimum thickness, range of thicknesses and maximum thermal neutron flux (E<0.5 eV) are given in Table I for various moderator materials. These are approximate values given to help determine the general dimensions of the moderator.

TABLE I

| | Moderator Thickness | | |
|---|---|---|---|
| Moderator Material | Optimum Thickness $d_3$ (cm) | Range of thickness $d_3$ (cm) | Maximum Flux (n/$cm^2$-sec) |
| HDPE | 6 | 4-10 | $7 \times 10^8$ |
| $D_2O$ | 15 | 9-25 | $2 \times 10^8$ |
| Graphite | 20 | 19-20 | $9 \times 10^7$ |
| $^7LiF$ | 25 | 20-30 | $3 \times 10^7$ |
| $AlF_3$ | 30 | 20-40 | $1.5 \times 10^7$ |

The calculation of the therapeutic ratio is also important and depends upon the organ in question (brain, liver) and the body mass of the patient. Although HDPE gives the highest flux, it gives a lower therapeutic ratio compared to $^7LiF$. The designer is expected to do calculations similar to this to determine the optimum geometry for the neutron irradiation system.

The MCNP simulation was used to determine the delivered dose and therapeutic ratio to the patient 58 and compare it to a planar neutron irradiation system. In one simulation, moderator 34 is composed of 7LiF whose thickness is $d_3$=25 cm. The inner diameter of the moderator (hole for head) is $d_4$=25 cm. The spacing between hemispheric fast neutron reflector 44 and hemispheric moderator 34 is $d_2$=10 cm. The head is assumed to be 28 cm by 34 cm. Fast neutron reflector 44 is made of $d_1$=20 cm thick lead in one embodiment. Thicker values of $d_1$ increase the tumor dose rate. At a thickness of 10 cm, the tumor dose rate is about one-half the value at a thickness of 50 cm. Fast neutron generators 68 are assumed to emit a total yield of $10^{11}$ n/sec. The combined titanium targets 52 give a total neutron emission area of 1401 $cm^2$.

In the MCNP simulation BPA (Boronophenylalanine) was used as a delivery drug. The concentration of boron in the tumor was 68.3 μg/gm and in the healthy tissue was 19 μg/gm. The calculated neutron dose rates in Gy-equivalent/hr are plotted in FIG. 5 as a function of distance from the skin to the center of the head. The calculated dose rates are comparable to those used for gamma radiotherapy, typically 1.8 to 2.0 Gy per session. For the same dosage, at a rate of 3 Gy-equivalent/hr, the session length would be from 30 to 40 min. long. These session times are considered reasonable for a patient to undergo.

Figure 6:
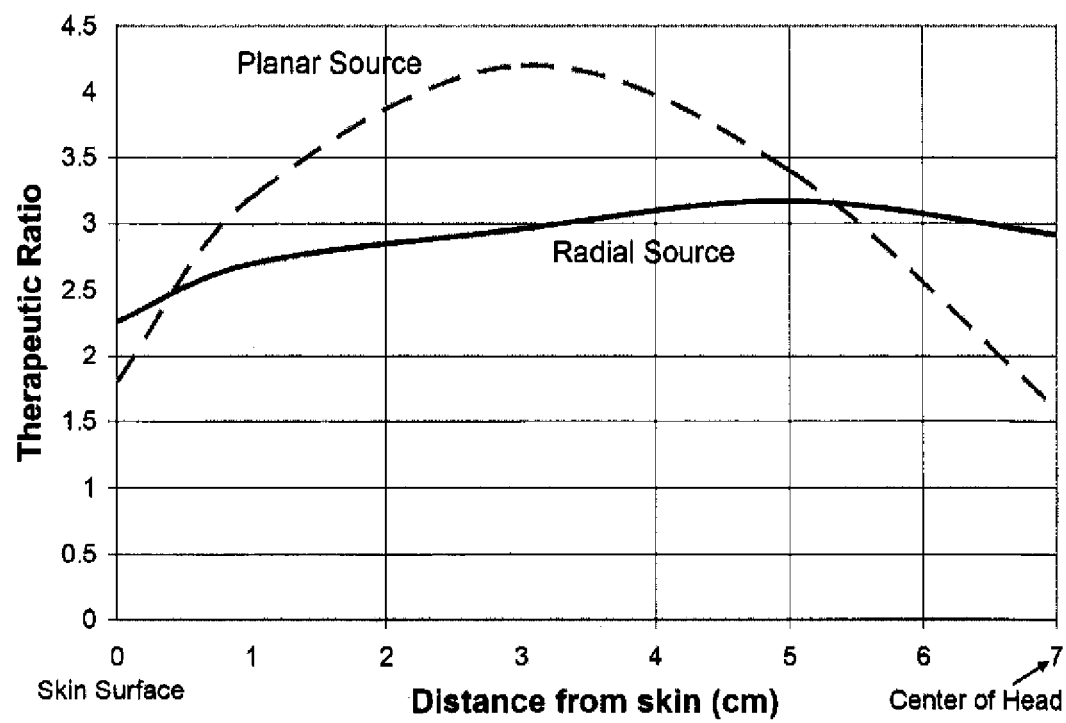
FIG. 6 is a graph of the therapeutic ratio as a function of distance from the surface of the head (skin) for the hemispheric (radial source) and planar moderator geometries in an embodiment of the invention.

For this simulation, the therapeutic ratio for the hemispherical neutron irradiation system is plotted in FIG. 6 as a function of distance from the skin to the center of the skull. The therapeutic ratio is defined as the delivered tumor dose divided by the maximum dose to healthy tissue. A therapeutic ratio of greater than 3 is considered adequate for cancer therapy.

Figure 1:
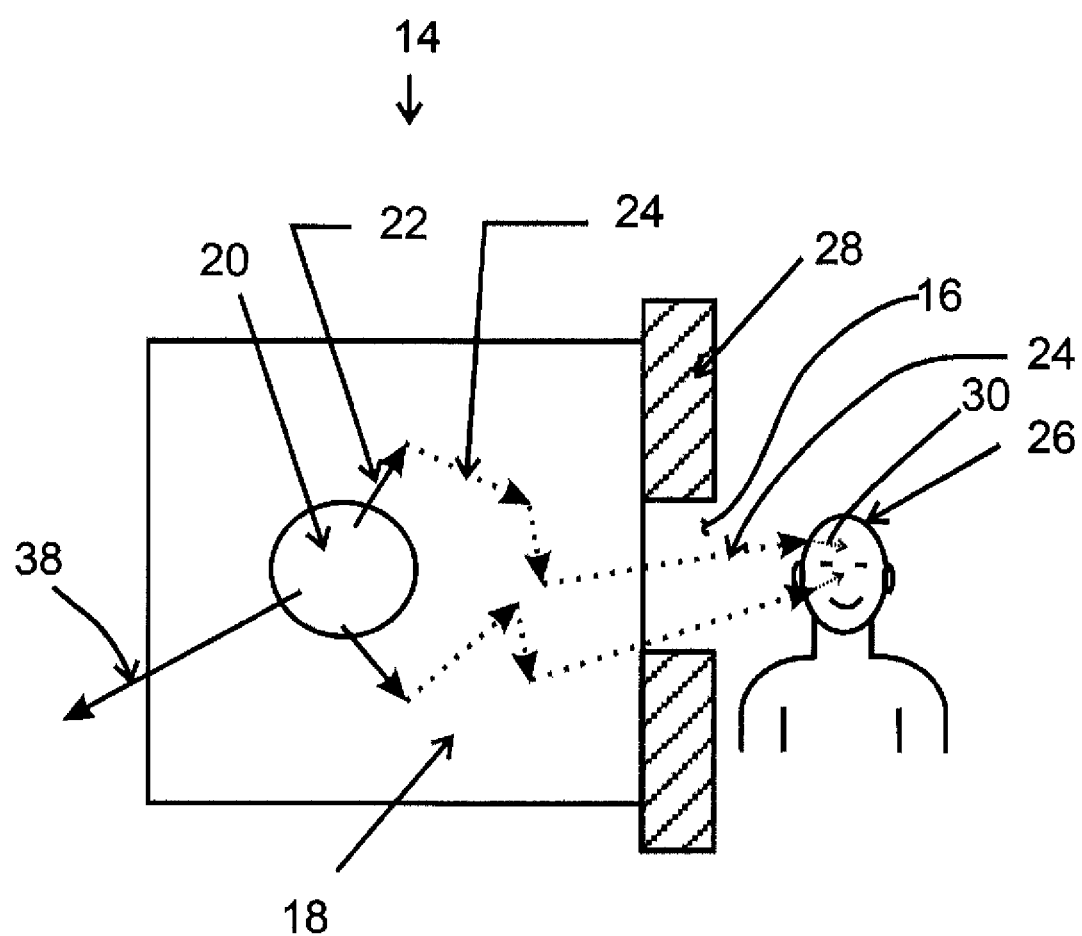
FIG. 1 (Prior Art) is a cross sectional view of a planar geometry for introducing thermal neutrons into a patient's brain.
Figure 5:
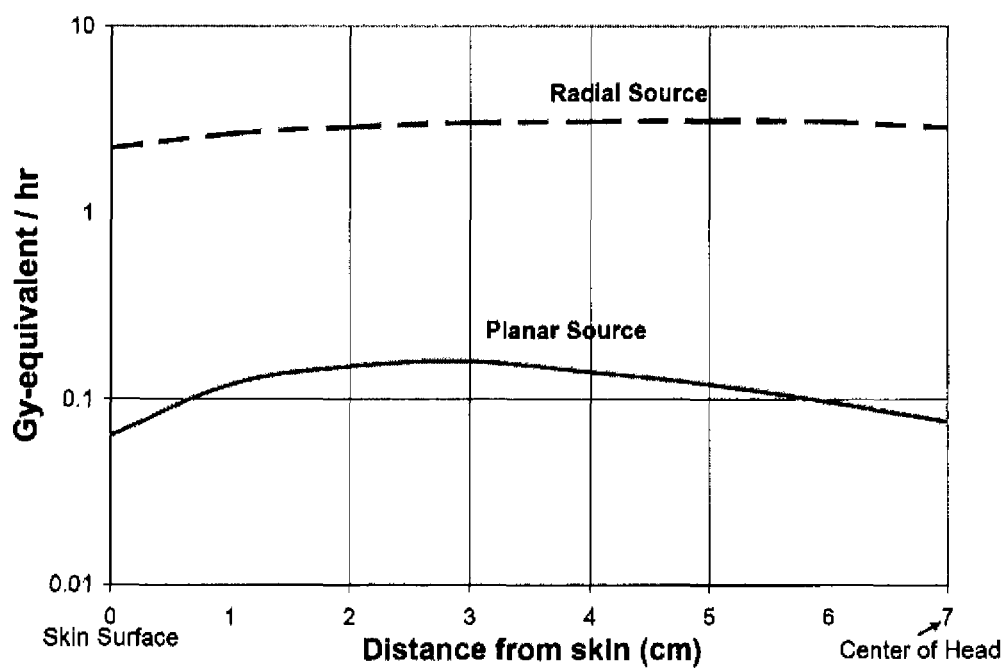
FIG. 5 is a graph of the dose rate (Gy-equivalent/hr) as a function of distance from the surface of the head (skin) for the planar and hemispheric moderator (radial source) geometries.

The conventional planar neutron irradiation system requires larger fast-neutron yields ($10^{12}$ to $10^{13}$ n/s) to achieve equivalent dose rates and therapeutic ratios. In FIG. 5, a planar neutron irradiation system 14 of FIG. 1 is compared with that of a hemispheric neutron irradiation system 36 (FIGS. 2, 3, 4) in one embodiment of the present invention, using the same source of fast neutrons ($10^{11}$ n/s). As can be seen from FIG. 5, the hemispherical neutron irradiation system (called radial source in FIG. 5) achieves a dose rate of about a factor of 20 over that of the conventional planar neutron irradiation system 14. The planar geometry needs a fast neutron source of $2 \times 10^{12}$ n/s to achieve the same results. Indeed, if a DD fusion generator is used, then the planar source requires a factor of 20× increase in wall-plug power or 2.0 MW, a prohibitively large power requirement.

In addition, as can be seen from FIG. 5, over a ± 5 cm distance across the head center, hemispheric neutron irradiation system 36 has less than a 10% variation in dosage. A uniform dose rate is crucial for the treatment of GBM, where we want to maintain a maximum therapeutic ratio and tumors may have distributed themselves across the brain.

Hemispherical neutron radiation system 36 in embodiments of the invention also gives a more uniform therapeutic ratio (FIG. 6) across the brain. The ratio is more uniform for the radial source and requires only $\frac{1}{20}^{th}$ of the fast neutron yield of the planar source (FIG. 1).

Other materials can be used for hemispheric moderator 34 in alternative embodiments. As those skilled in the art will know, high density polyethylene (HDPE), heavy water ($D_2O$), Graphite and $^7LiF$ can also be used. In addition, combinations of materials (e.g. 40% Al and 60% $AlF_3$) can also be used. Different thicknesses $d_1$ of moderator can be used to optimize the neutron flux and give the highest therapeutic ratio.

The term "neutron generator or source" is intended to cover a wide range of devices for the generation of neutrons. The least expensive and most compact generator is the "fusion neutron generator" that produces neutrons by fusing isotopes of hydrogen (e.g. tritium and deuterium) by accelerating them together using modest acceleration energies. These fusion neutron generators are compact and relatively inexpensive compared to linear accelerators that can produce directed neutron beams.

Other embodiments depend upon the selection of the plasma ion source that is used to generate the neutrons at the cylindrical target. These are (1) the RF-driven plasma ion source using a loop RF antenna, (2) the microwave-driven electron cyclotron resonance (ECR) plasma ion source, (3) the RF-driven spiral antenna plasma ion source, (4) the multi-cusp plasma ion source and (5) the Penning diode plasma ion source. All plasma ion sources can be used to create deuterium or tritium ions for fast neutron generation.
Cylindrical Irradiation System for the Liver and Other Cancer Sites.

Figure 7A:
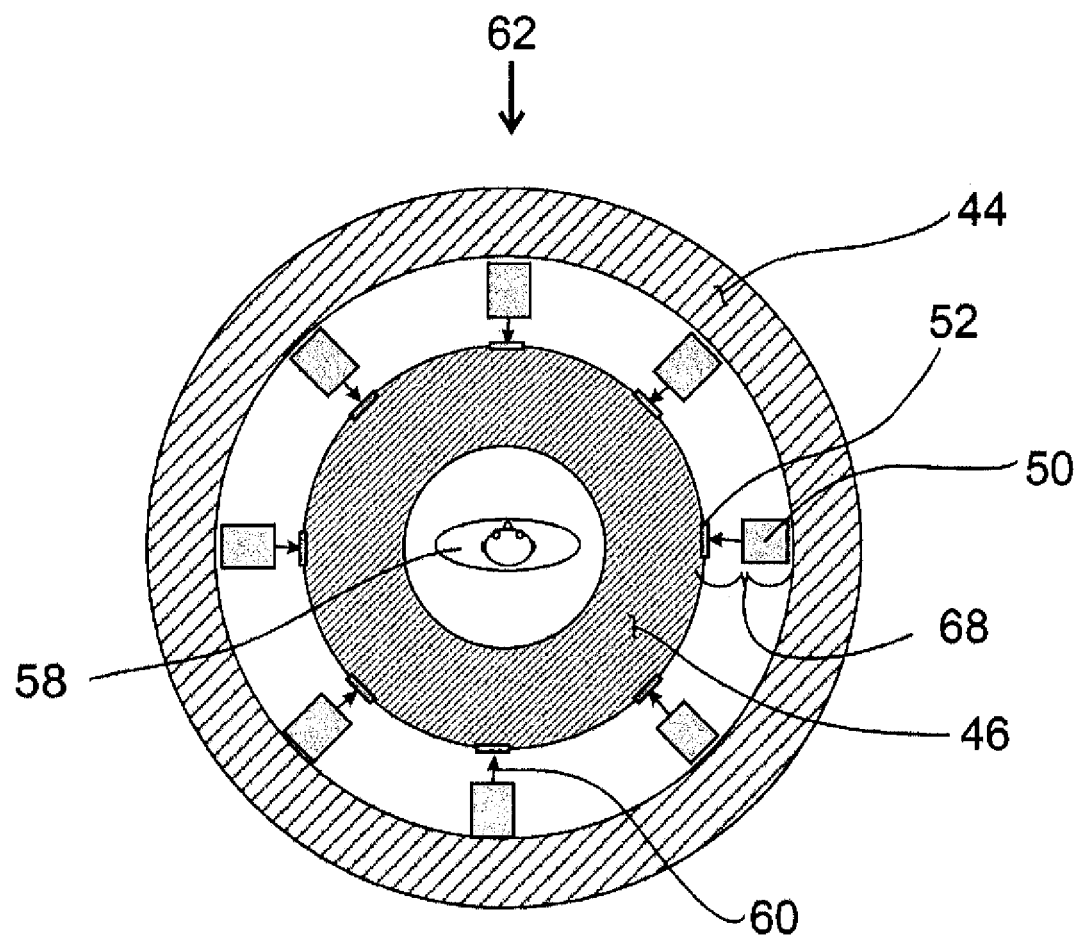
FIG. 7A is a cross sectional view of an embodiment of a cylindrical neutron irradiation system for the liver and other organs of the body.
Figure 7B:
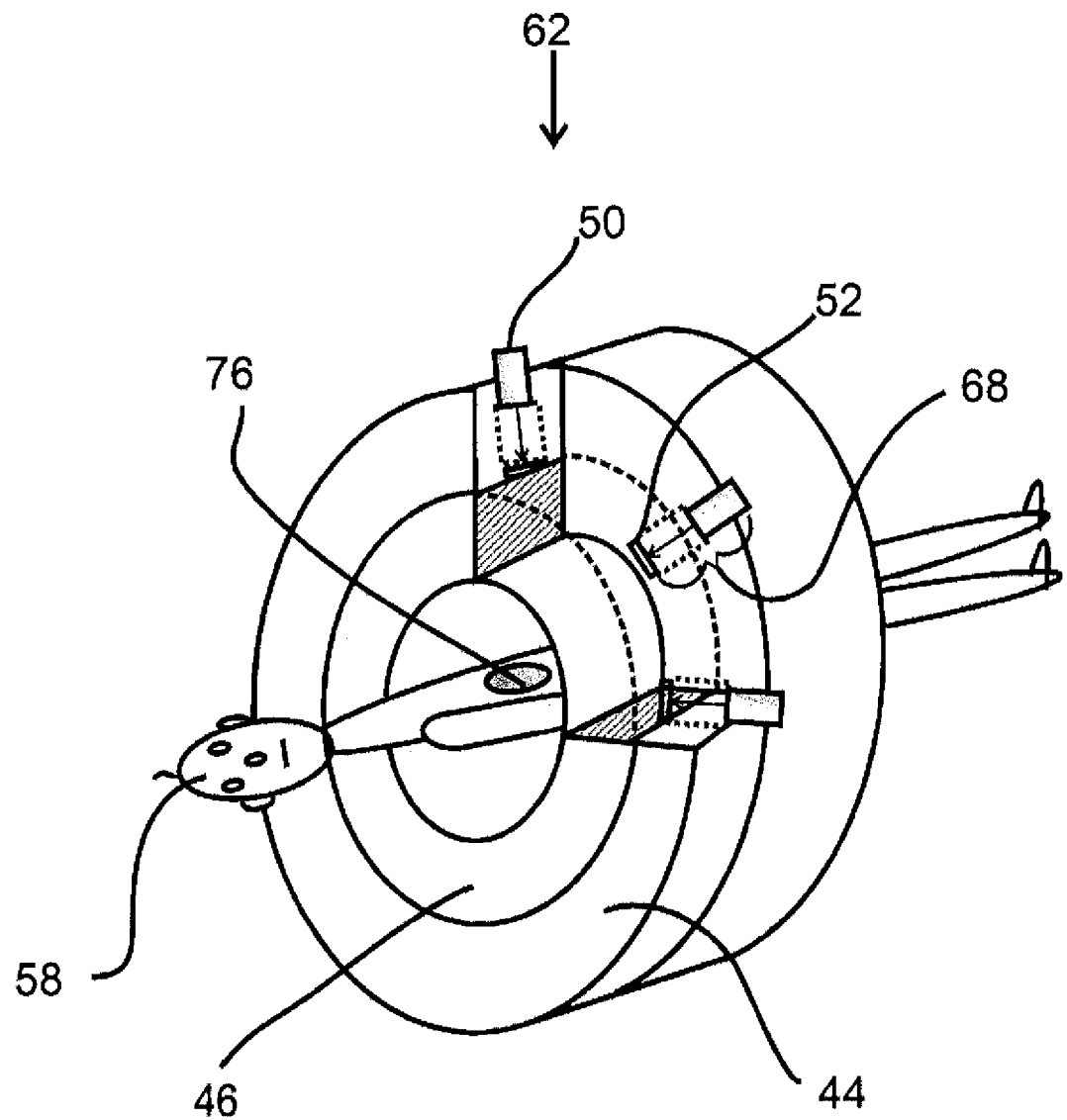
FIG. 7B is a perspective view of the cylindrical neutron irradiation system for the liver and other organs of a body.

FIGS. 7A and 7B shows another embodiment of the invention which uses a cylindrical geometry to irradiate other organs and parts of patient 58, such as the liver 76. FIG. 7A is a cross sectional view of cylindrical neutron irradiation system 62 and FIG. 7B is a perspective view of the same embodiment. In this embodiment eight fast-neutron generators 68 surround a cylindrical moderator 46. These generators 68 all emit their fast neutrons at the surface of the moderator. A cylindrical fast neutron reflector 44 surrounds the cylindrical moderator 46.

As in the case of the hemispheric moderator 34, the cylindrical moderator 62 can be composed of well-known moderating materials such as $^7LiF$, high density polyethylene (HDPE), and heavy water. These are shaped in a cylinder that surrounds the patient. The optimum thickness of the cylinder moderator for neutron capture purposes is dependent upon the material nuclear structure and density.

In this embodiment, fusion neutron generators are used to supply the fast neutrons. Fast neutron generator 68 is composed of a titanium target 52 and an ion source 50 as before. The titanium targets are contiguous to the cylindrical moderator 46. Ion beams 60 are accelerated using a DC high voltage (e.g. 100 kV) to the titanium target 52 where fast neutrons are produced from the DD fusion reaction. The fast neutrons are emitted isotropically from the titanium targets 52 on the moderator, some moving out to the fast neutron reflector 44 and others inwardly to be moderated immediately to epithermal or thermal energies. Those reflected come back into the cylindrical moderator 46 where they are moderated to epithermal and thermal energies, making their way finally to the patient 58.

Cylindrical neutron irradiation system 62 permits uniform illumination of a section of the patient's body (e.g. liver) as compared to the conventional planar neutron irradiation system. In the case of the brain, the body itself acts as part of the moderation process, thermalizing epithermal neutrons coming in from cylindrical moderator 46.

As one skilled in the art will realize, other cancers, such as throat and neck tumors, can be effectively irradiated by a hemispherical neutron irradiation system such as system 36. The thickness and material content of the moderator can be adjusted to maximize the desired energy of the neutrons that enter the patient. For example, for throat and neck tumors, the moderator can be made of deuterated polyethylene or heavy water ($D_2O$) to maximize thermal neutron irradiation of the tumor near the surface of the body. For deeper penetration of the neutrons one might make the moderator out of $AlF_3$, producing epithermal neutrons. These would be optimum for reaching the liver and producing uniform illumination of that organ.
Segmented Moderator In yet another embodiment, fast neutron sources with segmented moderators may be individually moved to achieve a uniform dose across the liver or other cancer site. This geometry produces a uniform thermal neutron dose with a factor of between $\frac{1}{10}^{th}$ and $\frac{1}{20}^{th}$ of the required fast neutron yield and line-voltage input power of previous linear designs. This again permits the use of the relatively safe deuterium-deuterium (DD) fusion reaction (no radioactive tritium) and off-the-shelf high voltage power supplies operating at modest power (<100 kW).

Figure 8:
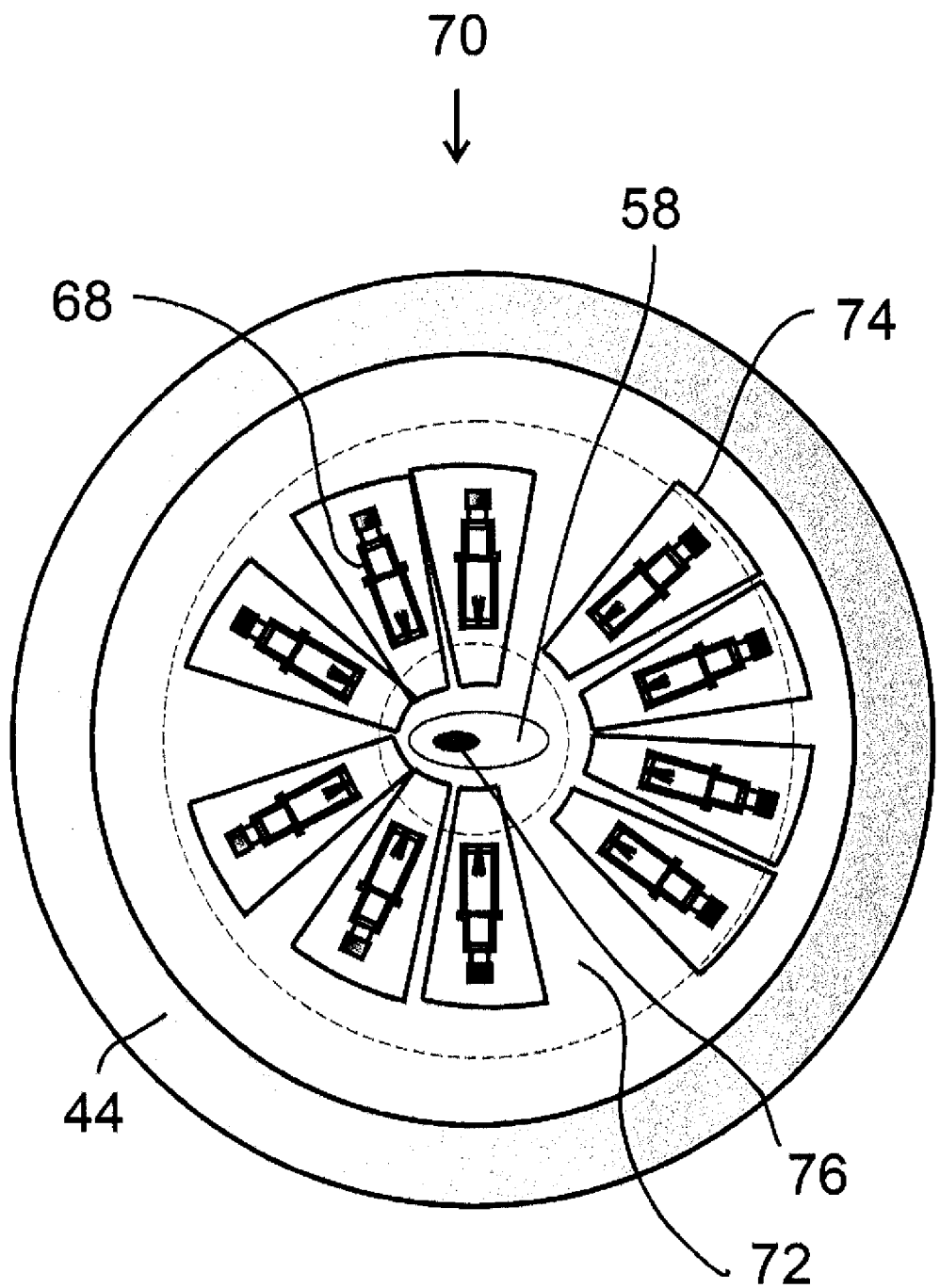
FIG. 8 is a cross sectional view of one of the embodiments of a neutron irradiation system wherein the neutron generators can be controlled independently to maximize thermal neutron flux at the liver or other organ of a body.

A segmented neutron irradiation system 70 in an embodiment of the invention is shown in FIG. 8. Ten fast neutron generators 68, each with a wedge-shaped moderator 74, surround the patient 58. The exact shape of each moderator can vary and can be of other geometries. Each generator and moderator pair can be moved independently of the others to achieve uniformity of the neutron flux across the liver, organ, or body part.

In between the wedge-shaped moderators 74 more moderating material ("filler moderating material" 72) is inserted, forming a large single moderator. The "filler" moderating material 72 can be heavy water or powered moderating materials such as $AlF_3$. Pie shaped fillers of moderating material can also be fitted into the spaces between the wedge-shaped moderator 74. Since neutrons scatter easily, there can be some space between the wedge-shaped moderators 74 and the pie shaped fillers without undue loss of neutron moderating efficiency.

The neutron yield from and the position of each fast neutron generator 68 can be adjusted to achieve uniformity across the liver or body part. The position and the neutron yield of the generator can be varied to achieve the desired radiation dose at a particular location in the patient's body. Since the cancer can be located in any part of the body, this benefit can be particularly useful for optimizing the dose at the cancer site.

Surrounding the entire fast neutron/moderator system is a cylindrical fast neutron reflector 44. Fast neutrons are produced by the fast neutron generators 68 and enter the moderators 74 where they are elastically scattered by collisions with the moderator atoms' nuclei, slowing them down after a few collisions to epithermal energies. As in the other embodiments, these epithermal neutrons enter the patient 58 and liver 76, wherein they are moderated further to thermal neutron energies.

The invention in various embodiments provides a uniform dose of thermal neutrons to the liver, organ or body part while minimizing fast neutron and gamma contributions. The required number of fast neutrons (e.g. $2\times10^{11}$ n/s) to initiate this performance is again reduced compared to that (e.g. $2\times10^{13}$ n/s) needed for the planar neutron irradiation system of the prior art.

Figure 9:
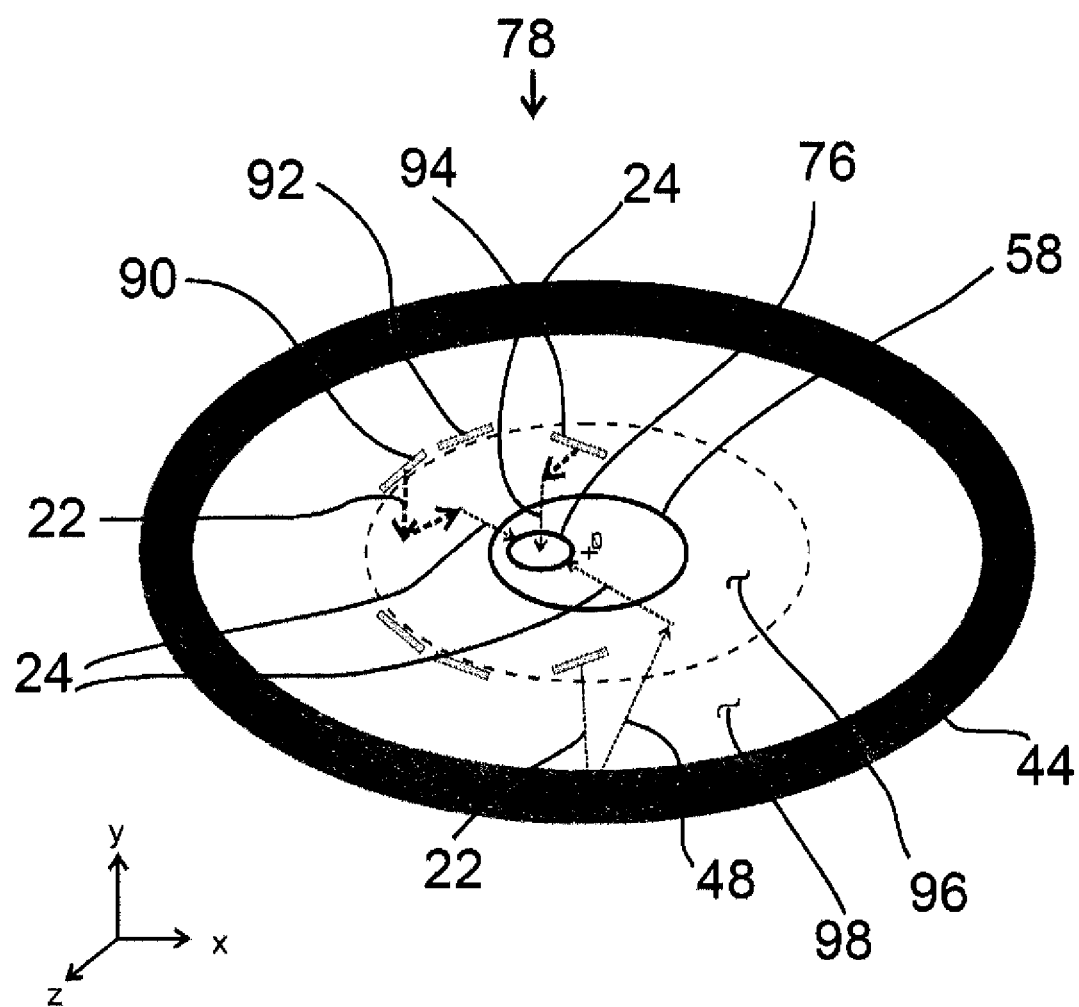
FIG. 9 is a simplified view of the cross section of the irradiation system that uses neutron generators that can be controlled independently of one another.

Another embodiment of the segmented design is shown in FIG. 9. The shape of the neutron irradiation system 78 is elliptical, with six sources of fast neutrons shown as distributed targets embedded in the inside elliptical moderator 96. Fast neutrons 22 are emitted isotropically in all directions. Those fast neutrons 22 moving outwardly are reflected back (see arrow 48) by fast neutron reflector 44, while fast neutrons traveling inwardly 22 are moderated to epithermal energies and enter the liver 76, where further moderation of the neutrons to thermal energies occurs. The inside elliptical moderator 96, outside elliptical moderator 98, reflector 44 and patient's body 58 act together to moderate and concentrate the thermal neutrons into the patient's liver 76. With a careful positioning of the moderators and fast neutron sources 90, 92, 94, a uniform dose can be achieved across the patient's liver, and, with a boron drug administered to the tumor, an excellent therapeutic ratio can be achieved.

Elliptical neutron irradiation system 78 in FIG. 9 is a simplified cross-sectional view of the patient 58 inside the elliptical moderator 96. This cross-section view is of a radial cut directly through the patient's torso and the moderator and fast neutron generator system. To maintain visual simplicity, only the titanium targets are shown and not the ion sources. Thus, six fast-neutron sources are represented by three flat titanium targets 90, 92, 94. The rest of the fast neutron generator is not shown. Other components (e.g. plasma ion source) are neglected in the analysis. The wedge-shaped moderators 74 (used in FIG. 8) are also not shown in FIG. 9.

For a simple simulation of the neutron irradiation system, the targets 90, 92, 94 are the sources of the fast neutrons and are arranged in an elliptical material 96 (e.g. $AlF_3$, LiF). The effect of the moderating material 96, the fast neutron reflector 44 and the patient's body 58 were calculated using a Monte Carlo N-particle (MCNP5) transport code to determine how fast the neutrons were converted to thermal neutrons in the neutron irradiation system.

Dosage calculations were made along a central axis of the liver. The fast neutron sources (titanium targets) are 2 cm×2 cm in area, each producing $10^{11}/N$ n/s, where N is the number of sources. The human body 58 dimensions are 35.5 cm along the major axis and 22.9 cm along the minor axis. The inner elliptical moderator 96 is made of $^7$LiF and 10 cm thick, while the outer moderator 98 is made of $AlF_3$ and 40 cm thick. The fast neutron reflector 44 is made of lead 50 cm thick. Boron-10 concentration is 19.0 μg/g in the healthy tissue and 68.3 μg/g in the tumor. The six sources are located in cms at: (−15, 18.06, 0) (−15, −18.06, 0) (−17, 17, 0) (−17, −17, 0) (0, 15.85, 0) (0, −15.85, 0). These measurements are made along the axis of the liver 76 from the point (−15, 0, 0) to (−5, 0, 0). In the x-direction, the first two sources 90 are centered about the left edge of the liver shown in FIG. 9, the two sources 92 are centered about the edge of the body, and the third two 94 are located above and below the origin. The origin is shown in FIG. 9 as a small cross + at the center of the body in the plane of the liver.

Figure 10:
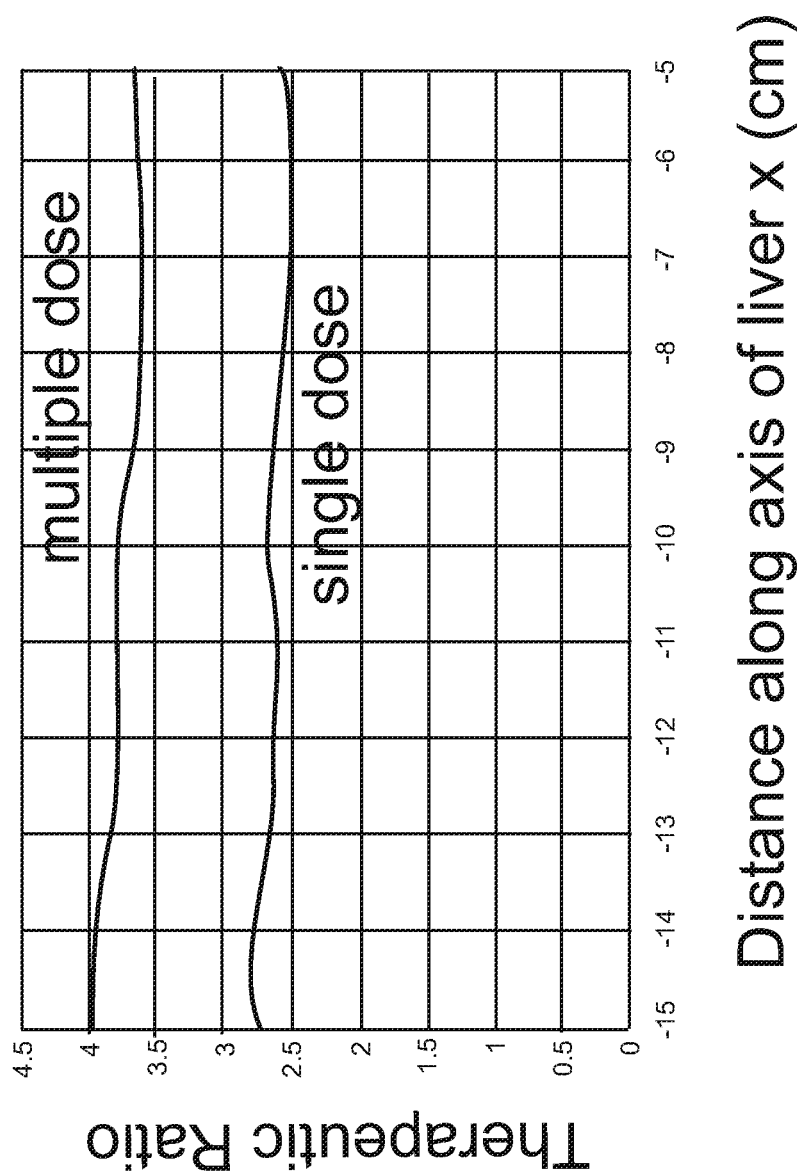
FIG. 10 is a graph of the therapeutic ratio as a function of distance along the axis of the liver in cm.

FIG. 10 shows the therapeutic ratio for a large single dose, and the therapeutic ratio for multiple small doses (where the photon dose to healthy tissue is not included) plotted as a function of distance along the axis of the liver. The photon dose can be neglected if there is some amount of time between doses. Many of the body's healthy cells can self-repair and recover between doses. The expected therapeutic ratio is between these two curves when there is fractionation into multiple doses. In this simulation, BPA was again used as the delivery drug with the concentration of boron in the tumor at 68.3 μg/gm and in the healthy tissue at 19 μg/gm.

Figure 11:
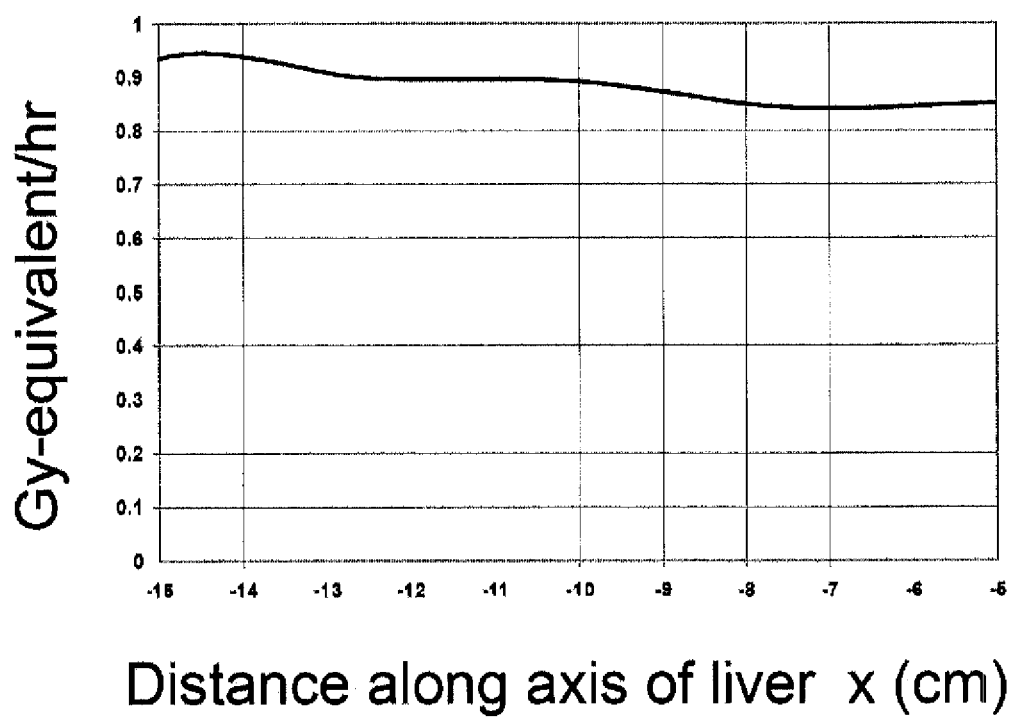
FIG. 11 is a graph of the dose rate as a function of distance along the axis of the liver in cm.

FIG. 11 indicates that the goal of having an extremely uniform dosage to the tumor has been achieved, with about ± 6% variation along the x-dimension. The calculated dose rates are comparable to those used for gamma radiotherapy, typically 1.8 to 2.0 Gy-equivalent per hour if we increase the total neutron yield to $2\times10^{11}$ to $3\times10^{11}$ n/s. Thus, at approximately $2\times10^{11}$ to $3\times10^{11}$ n/s it is possible to obtain a therapeutic ratio and uniform dosage to a tumor. Approximately 10 to 20 treatments of 30 to 40 minutes would be required, with a good therapeutic ratio, uniformity of dosage, and the opportunity for healthy tissue repair between treatments.

Once again, the planar neutron irradiation systems require high fast neutron yields to drive them. In one prior art system known to the inventors a fast neutron source of $3\times10^{13}$ n/s is needed to obtain realistic treatment time of ~1-2 hours. Using a D-T neutron source with a yield $10^{14}$ n/s, acceptable treatment times were obtained (30 to 72 minutes with single beam and 63 to 128 minutes with 3 beams of different direction). But these are impossible yields to achieve with realistic wall plug powers. Instead of 50 to 100 kW for the hemispheric and cylindrical neutron irradiation systems, it would take a minimum of 0.5 MW to achieve adequate yield for the planar geometry with a DT generator. These are high powers for clinics and hospitals.

As one skilled in the art knows, other cancers, such as throat and neck tumors, can be effectively irradiated by the neutron irradiation system. The thickness and material content of the moderator can be adjusted to maximize the desired energy of the neutrons that enter the patient. For example, for throat and neck tumors, the moderator can be made of deuterated polyethylene or heavy water ($D_2O$) to maximize thermal neutron irradiation of the tumor near the surface of the body. For deeper penetration of the neutrons one might make the moderator out of $AlF_3$, producing epithermal neutrons. These would be optimum for reaching the liver and producing uniform illumination of that organ.

Modular Generators

Introduction

As is shown in FIGS. 8 and 9, multiple modular generators may be encased in moderator material and may be arrayed to maximize thermal neutron flux at a cancer tumor location. Fast 2.5 MeV neutrons must be slowed (moderated) to energies (usually epithermal) that will penetrate to the cancer site without too many neutrons being lost in their travel to the cancer via capture by healthy tissue. These modular generators act as independent neutron sources and each may be optimized by adjustment of each individual beam's energy, direction and intensity. The modular generators can be arranged to fit a site in a particular subject's component location and structure. This is true also for cancer tumor location.

The energy of the neutrons can also be adjusted by adding or subtracting moderator material. This can be done more easily than with a single beam LINAC or reactor, which usually has a fixed beamline that is integral to the neutron source. In the prior art some adjustment can be made, but the DD fusion generator in embodiments of the invention, being much smaller, can have more degrees of freedom in direction, intensity and moderation. This has an added benefit of aiding physicians in tailoring neutron radiation to the patient's cancer.

Comparison to Linear Accelerators and Reactors.

Modular generators in various embodiments of the present invention may also form and be part of the mechanical structure of a cancer irradiation system. This has an added benefit of moving the neutron sources as close as possible to the cancer site and the diseased body part, resulting in efficient use of the neutron source. The neutrons are being emitted in a 4π solid angle from the modular generators, so the closer to cancer site, the more of the fast neutron flux is being utilized. Linear accelerators (LINACs), which are somewhat collimated, are further from the cancer site and cannot provide this advantage.

Compared to a linear accelerator, which can be several meters long or longer and may include large microwave power sources, the DD fusion sources in embodiments of the invention are less than one meter long and comprise compact microwave sources that can either be solid state microwave sources or small, inexpensive, single microwave oven magnetrons. The accelerator structure in embodiments of the invention is compact and includes a pre-moderator 118 that adds only from 5-10 cm of High-Density Polyethylene (HDPE) or 15-20 cm of polytetrafluoroethene (PTFE) Teflon to produce a first stage of neutron beam tailoring. The pre-moderator in these embodiments is an integral part of each modular generator, as is taught below with reference to several figures. In alternative embodiments other pre-moderator materials can be used such as $AlF_3$, $MgF_2$, $^7LiF$, and Fluental (trade name).

Smaller, Nontoxic, Less Complex Targets for Neutron Production

The modular DD fusion generator 118 in embodiments of the present invention uses a small titanium target (e.g. a 5 cm diameter disk of titanium backed by water-cooled copper fins) to produce neutrons. The target is supported directly on the pre-moderator, which is an integral part of the apparatus in this application, termed a modular generator. Linacs and other methods in the conventional arts use larger or toxic targets that require complex cooling and rotation. For example, the neutron source used by Neutron Therapeutics has a 2.6 MeV electrostatic proton accelerator and a rotating, solid lithium target for generating neutrons. In that prior-art process the Lithium becomes radioactive and toxic, and when exposed to air, it disintegrates. This prior art source has a large target chamber housing a large Li disk which is rotated in a powerful 2.8 MeV proton beam produced by a large accelerator. The Lithium wheel is roughly 2 meters in diameter and has been divided into pie-shaped sections that are removed by mechanical robotic means. In embodiments of the present invention, the Ti target is a relatively small diameter (~5 cm) and is typically attached with 6-8 screws to the pre-moderator block and is sealed to the block with a Viton "O" ring. The Ti targets in embodiments of the invention can be easily manually removed and replaced. They also have a long lifetime and have been tested for over 4000 hours with no failures.

Nuclear reactors are large structures with a substantial amount of shielding (water and concrete) and cooling systems to maintain the hot reactor core. Reactors provide primarily thermal neutrons that must be raised up in energy using an energy multiplier, and then the neutron beam must be improved to IAEA standards to produce epithermal neutrons with minimal gamma radiation.

Optimizing Neutron Energy for Penetration and Minimum Damage to Healthy Tissue

For tumors at depths in a subject of 3 cm or more, a goal for the moderator is to provide a neutron beam that has its energy clustered about 10 keV at the skin, in order to provide sufficient energy to penetrate a minimum of several centimeters into a human target while avoiding higher energies that are more damaging to human tissue. High conversion to epithermal energies occurs in HDPE at a thickness of approximately 5 cm, but it also produces a high yield of thermal neutrons and 2.2 MeV gammas that can damage the healthy tissue at the skin.

Modular Generators

In embodiments of the present invention modular generators are very important components. The modular generator combines multiple functions that were separate functions in the prior art. These integrated functions include both neutron production and beam tailoring. FIG. 12A is a perspective view of an individual modular generator 118 in an embodiment of the invention.

Figure 12B:
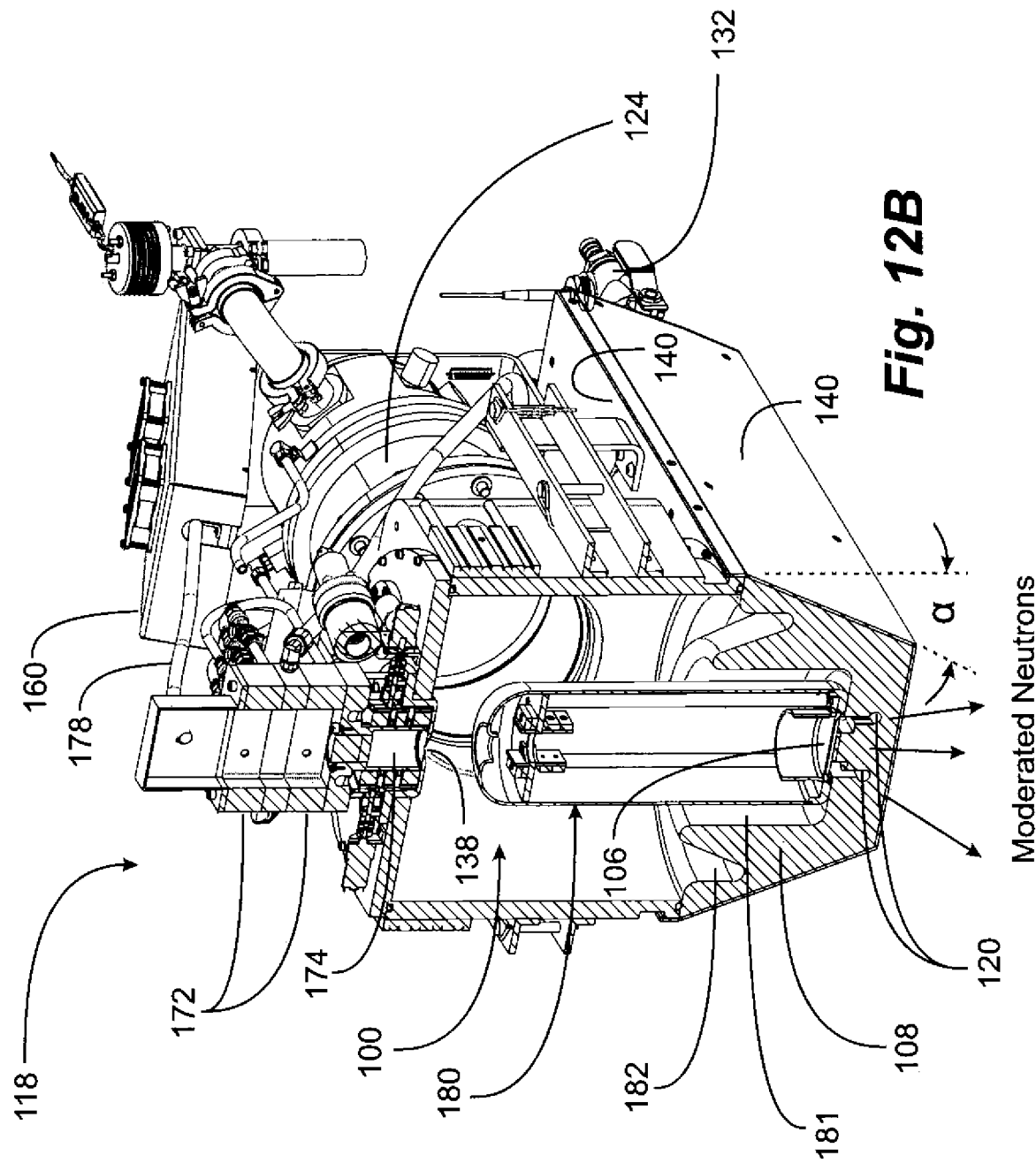
Figure 12C:
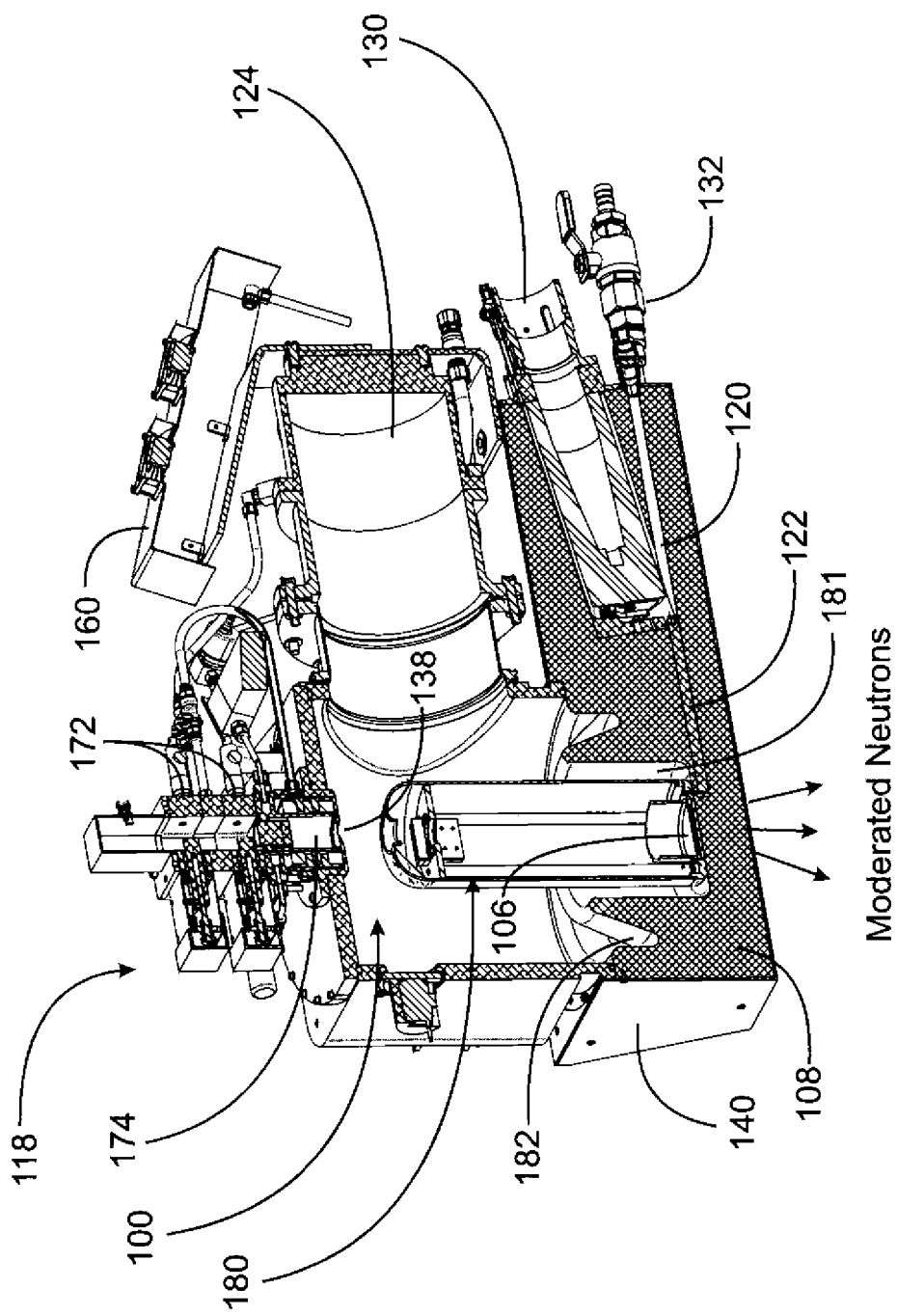

FIG. 12B is a cross section of the modular generator 118 of FIG. 12A taken along an axis of an acceleration chamber 100 for ion beam generation and containment, and at a right angle to the axis of a turbo vacuum pump 124 that is part of the modular generator 118. FIG. 12C is a cross section of the modular generator 118 of FIG. 12A taken along the axis of the acceleration chamber 100, and along the axis of the turbo vacuum pump 124, at a right angle to the section of FIG. 12B. Each modular generator 118 can operate independently of the other modular generators and each possesses all required components to generate neutrons. Further, the various modular generators may have pre-moderators shaped to engage other building blocks of a project, such as adjacent generators or spacing moderators, as is described in enabling detail below.

Viewed as in FIGS. 12A, B and C, each modular generator 118 comprises a pre-moderator 108 that is made of material known to moderate energy of energetic neutrons. In most embodiments the pre-moderator is a solid block of material, with a rather complicated shape for certain purposes. Modular generator 118 has three key elements: (1) a deuterium ion source 102, (2) an acceleration chamber 100, through which deuterium ions may be accelerated, and (3) a titanium target 106 (shown in FIGS. 12B and 12C) that is bombarded by the deuterium ions to produce high-energy neutrons. The deuterium ion source 102 has an attached microwave source 160, and microwave slug tuners 172, connected by a cable 178. Deuterium gas is leaked slowly into a plasma ion chamber 174 at the upper end of the acceleration chamber, where microwave energy ionizes the gas, creating deuterium D+ ions.

The gas is ionized by microwave energy, and Deuterium (D+) ions are created and accelerated out through an ion extraction iris 138 into acceleration chamber 100, and through an electron suppression shroud 180 which deflects back-streaming electrons from being accelerated back into the plasma source, which could damage the apparatus. Electrons are being created by collisions of the D+ ions in the deuterium gas that are being created in the acceleration chamber.

The deuterium ions are positively charged, and target 106 is negatively charged to a level of from 120 kV to 220 kV, and the D+ ions are strongly attracted to negatively biased target 106. Acceleration chamber 100 is connected to a turbo vacuum pump 124 that provides a modest vacuum in one embodiment of about $10^{-6}$ Torr, minimizing scattering of the $D^+$ ions as they travel from the extraction iris 138 to the target 106. Titanium target 106 is positioned in a primary electrically insulating well 181 at the bottom of the chamber embedded into the pre-moderator material, which may be UHMW, HDPE or Teflon, of the pre-moderator 108. There is further a secondary electrical insulating well 182 surrounding the primary electrical insulating well. The surface of the moderator material in the primary and secondary electrical insulating wells may be seen as a corrugated insulator causing any surface charge to follow a curved path taken in any direction. The purpose is to provide a very long surface path to prevent electrons from traveling from the target to acceleration chamber 100 wall or any grounded element, and to avoid surface electrical breakdown or flashover in that surface path. As those skilled in the art know, the wells form an electrical insulating path. Additional corrugations or wells can be added to lengthen the path.

Pre-moderator 108 has a high voltage bus bar 122 and fluid cooling channels 120 to and from the target. The high voltage is introduced via a high voltage receptacle 130 which is connected to the high voltage bus bar. Pre-moderator 108 acts as a HV insulator and as a mechanical support for the target 106 at a high negative bias. The pre-moderator 108 has metal cladding 140 at ground potential to minimize high voltage breakdown through the pre-moderator plastics. When in operation the $D^+$ ions in the ion beam are attracted to the titanium target 106, where fast (2.5 MeV) neutrons are produced in a resulting DD fusion reaction.

Figure 13A:
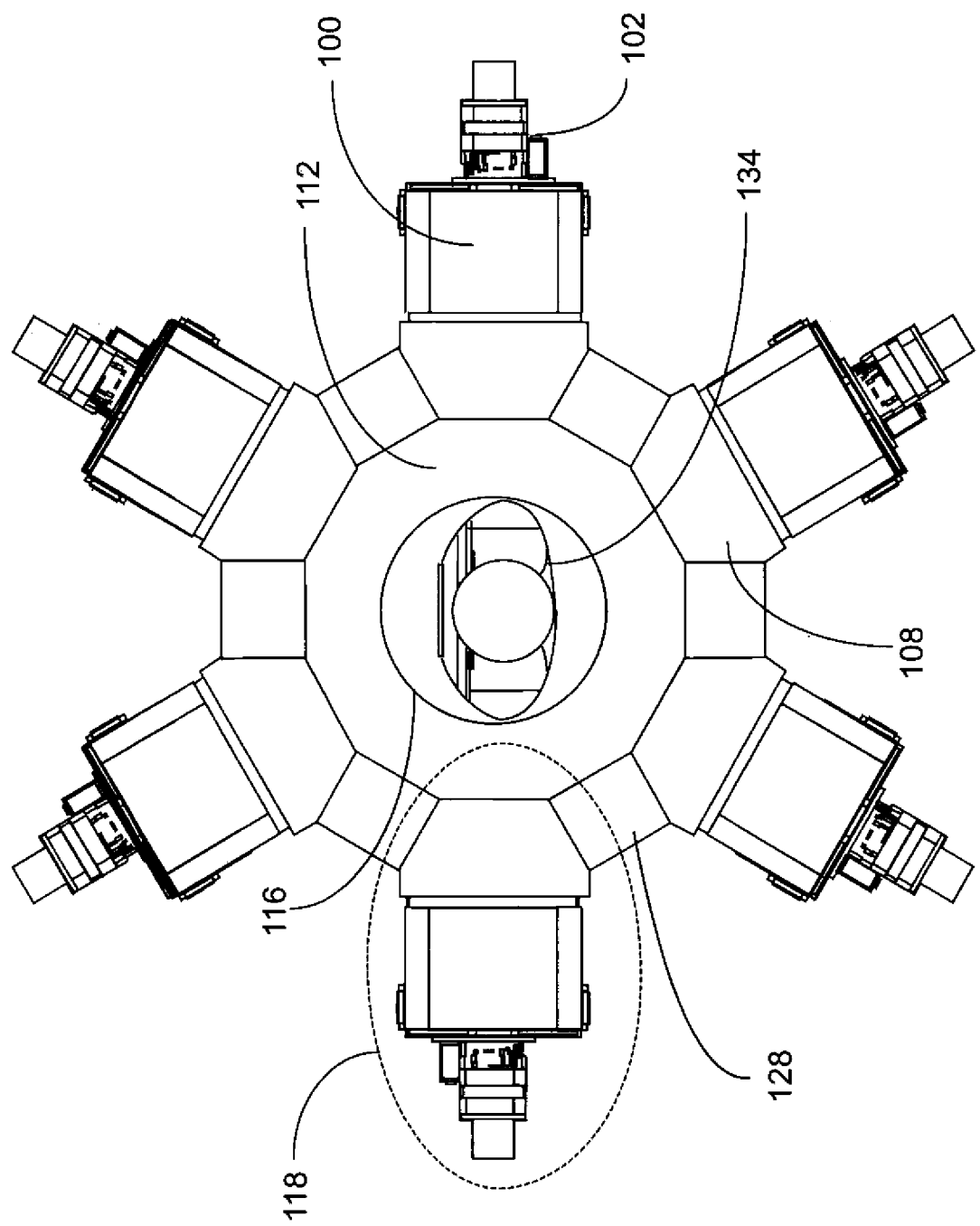
Figure 13B:
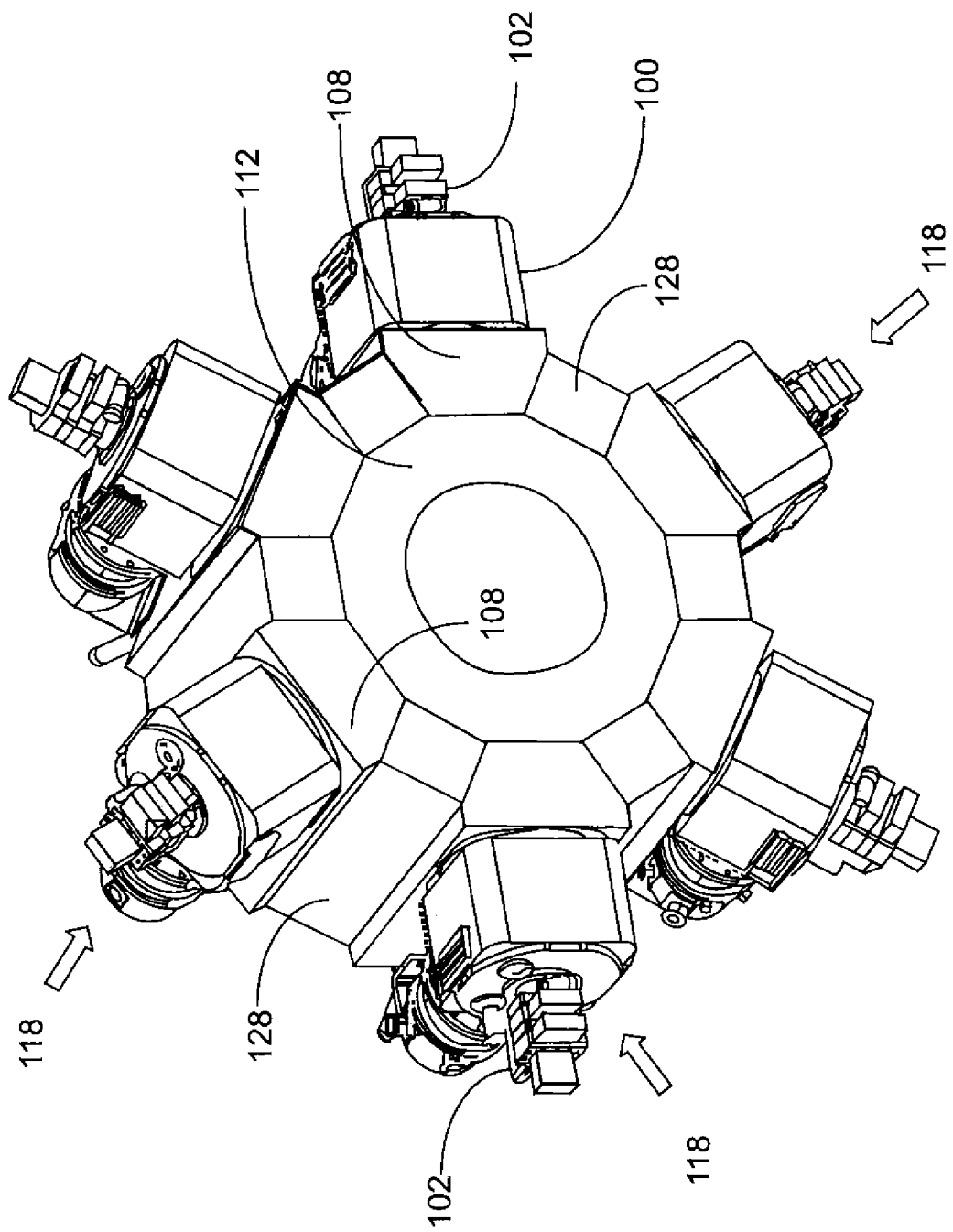
Figure 13C:
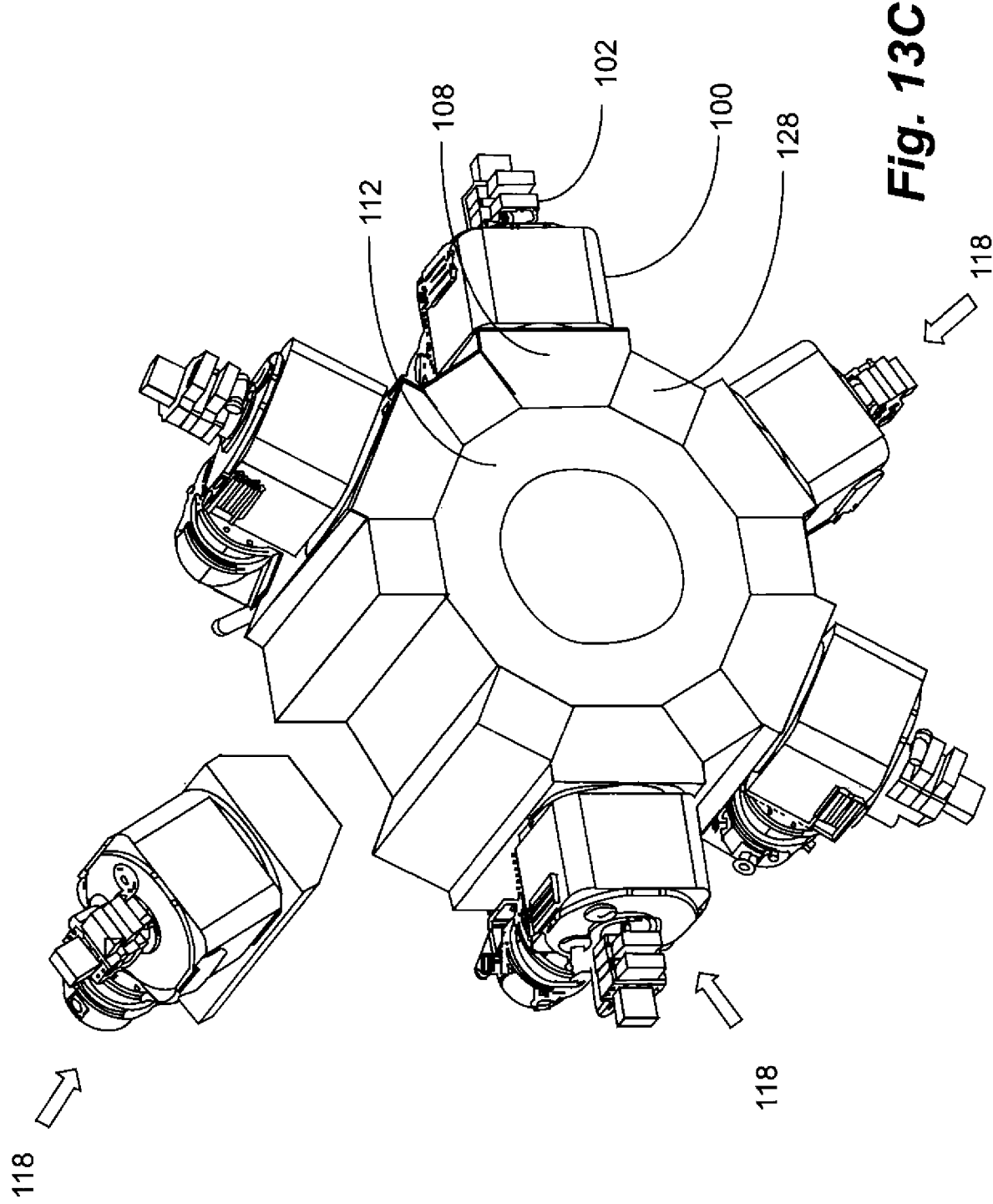
Figure 13D:
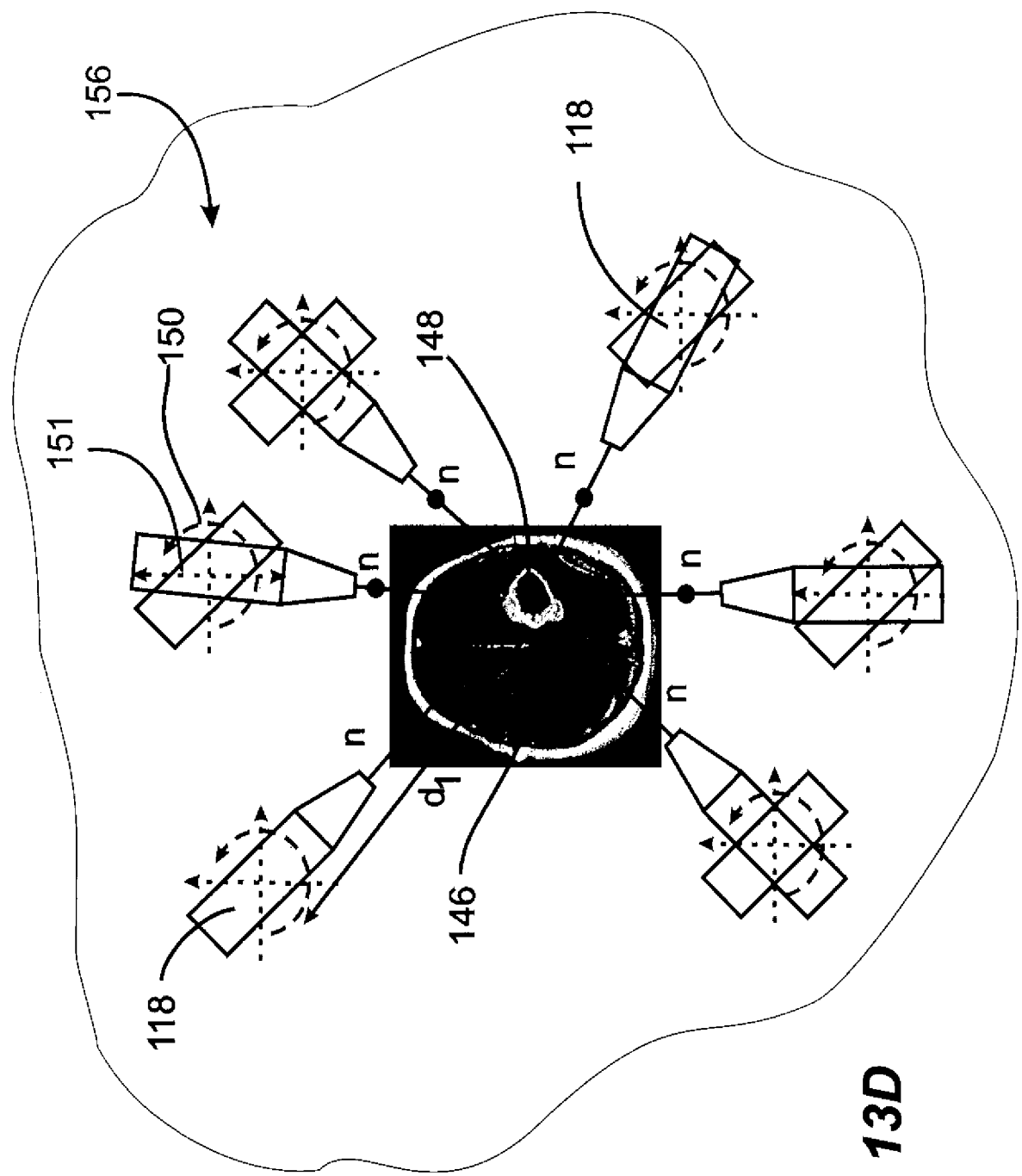

FIG. 13A illustrates an assembly of six modular generators 118, wherein pre-moderators 108 are spaced apart by spacers 128 which are also made of moderator material. FIG. 13B shows the arrangement of FIG. 13A in perspective. FIG. 13C shows the arrangement of FIG. 13B with one modular generator 118 removed from the assembly. FIG. 13D is a more diagrammatic illustration showing an arrangement in which modular generators may be mounted on translation and rotation mechanisms to be positioned to maximum irradiation of a cancer site. As is shown in FIGS. 13A-D the modular generators in embodiments of the invention may be arranged in an array to form a complete and moveable system of irradiating neutron sources with pre-moderators. For example, as shown in FIG. 13A-C, in the simplest configuration of the array, the modular generators may form a circle around a human torso or body part. The modular generators can be moved into three dimensional arrays around the subject to maximize neutron flux to a cancer site 148 that may not be centered on a body part 146, illustrated as a human brain in FIG. 13D. Thus, depending upon body contour, shape and size, and cancer location and distribution, the modular generators may be moved to adapt to the shape and tumor location in order to maximize the dose to the cancer and to minimize the dose to the other body parts. Referring to FIG. 13D, rotation 150 and translation 151 of the modular generator 118 can be achieved with electrical motors attached to the modular generator 118.

Seven Functions of the Pre-Moderator

Because the titanium target is on the pre-moderator (first stage of moderation), fast neutrons coming from the target immediately enter the pre-moderator and quickly moderated to thermal or epithermal energies. The pre-moderator also provides mechanical support, high voltage supply and cooling fluid transport to the titanium target. Exemplary pre-moderator materials that may accomplish this are Teflon and HDPE. Both Teflon and HDPE are excellent high voltage dielectrics which can also support a HV bus bar 122 and water channels 120 to be used to transport HV and the cooling fluids to the Ti target, as shown in FIG. 12C. As shown in FIGS. 12A, B, C a single generator 118 consists of an acceleration chamber 100, an ion source 102 emitting deuterium ions, a titanium target 106 and a pre-moderator 108. Pre-moderator 108 also provides a function of being a high voltage insulator for high voltage bus bar 122 that delivers high voltage (e.g. 80 kV to 300 kV)) to titanium target 106, and a water channels 120 that deliver cooling fluid to the titanium target 106. The high voltage is delivered from a high voltage power supply through a standard HV receptacle 130 to the bus bar 122 and then on to the titanium target 106, all of which are mounted in the pre-moderator 108.

In various embodiments of the invention the pre-moderator 108 performs seven functions: (1) moderation, (2) mechanical support of the titanium target, (3) cooling fluid transport to the target, (4) high voltage transport to the target, (5) minimum surface flashover, (6) and a portion of a high vacuum container (a wall) with no out gassing (7). These seven attributes permit a substantial reduction of distance and amount of material between the fast neutron source and the patient, thus helping to maintain a maximum neutron flux delivered to the patient.

Modular Generators Around a Subject

FIGS. 13A-D show how the generators may be arranged. In FIG. 13A, six modular generators 118 form a ring around a secondary moderator 112 and are part of a structure formed by secondary moderator 112, spacers 128, and pre-moderators 108. Pre-moderators 108 and secondary moderator 112 provide the moderation function by slowing the neutrons down to epithermal energies (function #1). These elements also form a mechanical support (function #2) for the entire generator and moderator system.

Secondary moderator 112 may also be a separate section attached directly to the modular generator just after the pre-moderator, each separate from the other instead of being in a ring 112 as in FIG. 13A.

As shown in FIG. 12B-C, fluid transport (function #3) is supplied through channels 120, which delivers cooling fluid to target 106 to maintain the target at an acceptable operating temperature. Each generator is supplied with a separate cooling fluid input and output, wherein cooling fluid is provided through a connector 132 shown in FIGS. 12A-12C. Thus, the pre-moderator supplies fluid transport (function #4). High voltage is delivered via high voltage bus 122, which passes through pre-moderator 108 (function 4, high voltage transport). HDPE, UHMW and Teflon are excellent insulators and withstand high voltage flashover (function #6). All three may be used in vacuum systems without excessive out gassing and may help maintain the system vacuum (function #7). The achievement of these seven functions provides a very compact and flexible neutron source.

The Secondary Moderator

Secondary moderator 112 (FIGS. 13A-C) may comprise any one of or a combination of multiple moderator materials that optimize both the maximum flux and neutron energy for maximum dose to the cancer site. Selection (material, size and shape) may be varied depending on depth of the cancer in the subject and a desired dose at the cancer site. The secondary moderator may be $D_2O$ (heavy water) for delivery of thermal neutrons to, for example, throat and neck cancers, or a combination of $AlF_3$ and Teflon for delivery of epithermal neutrons to brain tumors. The recommended levels of fast, thermal and gamma emission by IAEA are given in Table I.

TABLE 1 values in window.
IAEA Recommended the beam exit

| BNCT beam port parameters | IAEA Recommended value |
|---|---|
| $\phi_{epithermal}$ (n cm$^{-2}$ s$^{-1}$) | ~$10^9$ |
| $\phi_{epithermal}/\phi_{fast}$ | >20 |
| $\phi_{epithermal}/\phi_{thermal}$ | >100 |
| $D_{fast}/\phi_{epithermal}$ (Gy cm$^2$) | <2 × 10$^{-13}$ |
| $D\gamma/\phi_{epithermal}$ (Gy cm$^2$) | <2 × 10$^{-13}$ |
| Fast energy group ($\phi_{fast}$) | E > 10 keV |
| Epithermal energy group | 1 eV ≤ E ≤ 10 |
| Thermal energy froup ($\phi_{thermal}$) | E < 1 eV |

These IAEA recommended values depend upon older drugs, such as p-Boronophenylalanine (BPA) that have been approved for use in humans by the Food & Drug Administration (FDA) for other medical applications. Delivery of higher boron concentrations to a cancer site may depend to some extent on newer drugs to be developed, and may permit lower power, less efficient neutron beams to be used. Since treatment time might also be faster, the neutron beam quality need not be as high. DD fusion generators in embodiments of this invention have relatively low beam flux, thus permitting them to be used for cancer therapy.

In some embodiments multiple modular generators may be distributed around a secondary moderator surrounding a central chamber holding a subject for treatment, providing an alternative to a completely integrated multi-ion beam system, and may have particular benefits in some circumstances. Benefits might include (1) an ability to quickly replace a single generator that has failed and needs repair; and (2) an ability to change alignment of the generators relative to one another, the moderator, and the subject. In regard to a subject, alignment of the generators may optimize dose distribution and density of neutrons at a cancer site, while at the same time minimizing spurious radiation, such as gamma rays that might be emitted external to the apparatus, or into healthy tissue of the subject.

In the prior art, where reactor and accelerator neutron sources are used, careful attention has been given to achievement of high quality neutron beams to meet the IAEA standards for BNCT developed in 2001 for International Atomic Energy Agency (IAEA) (Current Status of Neutron Capture Therapy (2001) IAEA-TECDOC-1223. In embodiments of the present invention, where multiple modular DD fusion generators are used, these standards may be relaxed. The IAEA specification assumes that there is a single neutron beam that is used for all cancers and body locations. This results in standard values for the three neutron energies (thermals, epithermal and fast neutrons). Moderator and neutron spectral shifters are then designed to achieve these values for a particular fast neutron source as an input specification. This results in designs in the prior art that may not use the available fast neutrons economically and then may waste some of them to achieve the IAEA universal specs. For generators such as the DD fusion source in an embodiment of the present invention, early calculations have indicated that a single DD fusion generator would have difficulty achieving required fast neutron input to the moderating process. So, in embodiments of the invention, the use of multiple generators increases the total fast neutron yield available and allows the moderated dose to be distributed over a larger area of the body, instead of having the beam enter at one location of the body. For example, as shown in FIG. 13D, neutrons n are entering the head from many directions. This permits reduction of thermal neutron flux at any one point on the skin of the head while still achieving adequate epithermal flux to the cancer site. In early prior art reactor BNCT experiments, the thermal neutron flux burned the skin of subjects.

When considering neutrons used for a particular cancer it is desirable to direct the maximum flux to the cancer site, and therefore, one must consider the specific cancer that is to be treated. This includes location and depth in the human body. Because of their relatively small size and large neutron yield, the modular generators in the embodiments of the present invention are particularly able to accomplish this by being positioned to maximize their flux at the cancer site.

Since in embodiments of the invention generators are placed as close to the patient's body as practical to maximize flux at the cancer site, there is a more holistic problem. There are multiple parameters for each modular generator: (e.g. neutron flux, neutron energy, position relative to the body). What comes out of a single neutron beam pipe (1998 IAEA Standards, Table I) is not the only concern. A body part can now, in new implementations of the invention, be irradiated in all directions, and neutron intensity can be adjusted at each modular generator to achieve better flux and even more optimum neutron energy than with a single beam LINAC or a reactor. The direction of each neutron beam can be adjusted by rotating and displacing each modular generator 118. Each modular generator's yield can be adjusted electronically by varying the accelerator voltage and the ion beam current. Since the moderator size is relatively small and compact compared to the prior art, the neutron spectrum of each modular generator 118 can be adjusted by the selection of different moderator materials and thicknesses.

Lowering of Required Beam Quality

In embodiments of the present invention the subject's body is bombarded with neutrons from multiple directions. The neutrons can come from all sides of the body part, which minimizes the amount of distance each beam has to transverse. Unwanted neutrons striking the skin are now distributed over a larger area, reducing the skin dose of harmful components (e.g. gammas, and thermal and fast neutrons) per unit area. These components are simply delivered over a larger area of the skin. This permits adjustment of dose at the cancer site to be higher than that achieved with a single beam but with reduction of harmful components over a larger area of the skin.

For a single beam case in the prior art, an argument might be made that one can rotate the patient for each exposure, but, due to possible patient movement, the neutrons would not be as accurately placed as in multi-beam embodiments of the present invention. For each placement the patient would have to be carefully re-oriented relative to the single neutron beam, which requires careful placement of the patient.

In embodiments of the invention, multiple beam directions and an ability to adjust the neutron flux of each modular generator allow for optimum delivery to the cancer site while reducing harmful components. For example, if the cancer is located in the left lobe of the brain, the neutron flux to the tumor can be adjusted to deliver epithermal neutrons in the direction of that tumor. Since each modular generator neutron flux can be adjusted quickly by varying the accelerator's high voltage or the ion beam current, and by translation and rotation, this can be done easily with delivery determined by a computer program. In the present invention, a control computer monitors the ion beam current, the acceleration voltage and the output neutron yield, which can be automatically adjusted.

Small modular generators in embodiments of the invention can make use of new boron drug delivery methods for higher concentrations of boron to the cancer sites. Higher concentrations of boron lower the required neutron dose and require shorter delivery time. Higher boron concentrations to the cancer site permit use of neutron generators with lower neutron yield such as the modular DD fusion generators in embodiments of the present invention.

Each modular generator 118 is an independent device capable of producing neutrons independently of the other generators. This allows the total available power, P, to be distributed over N generators, resulting in the heat load being distributed safely without, for example damaging the titanium targets (unlike single target devices using lithium). In one example there are six modular generators, distributing total heat load per titanium target, since the number of neutrons per unit area is fixed by the ion beam power per unit target area.

To properly treat a tumor in a subject, a large number of neutrons is required. For reasons of temperature management and stability, DD fusion generators are at present limited to fast neutron yields of less than $4 \times 10^{10}$ n/sec. To increase the neutron yield, the number of neutron generators can be increased in embodiments of the present invention. Pre-moderators 108 can be shaped so that larger numbers of modular generators may be fitted around a subject to be treated. In the example shown by FIG. 13A there are six generators arranged equally spaced around a common secondary moderator 112, the subject cavity 116 and the subject 134. Spacing blocks 128, composed of moderator material that may be the same as that of pre-moderator 108 (e.g. Teflon or polyethylene), are placed between each pre-moderator to provide adequate spacing for fitting the subject cavity 118. The wedge angle, α, as indicated in FIG. 12A, on the pre-moderator in FIG. 13A determines the number of modules 118 with pre-moderators 108 that can fit in the circle around the patient and how close the sources may be to the patient. For example, a wedge angle of α=30° for 6 generators and α=22.5° for 8 generators.

Moveable Sources with Fluid Moderator

One embodiment of a system of modular generators is shown in FIGS. 13A and 13B. In FIG. 13A a plane view of six modular neutron generators 118 fitting into the cylinder (or ring) is shown. In FIG. 13B, a perspective view is shown. The modular generators can also be arranged in other patterns to maximize the dose in particular locations in the subject's body and deliver cancer therapy to selected body organs. In some embodiments of the invention the modular generators may be moved by electric motors and mechanical means to optimized locations to provide the maximum dose to the cancer site and tumor profile as determined by boron bio-distribution test biopsy and pathological analysis, Positron Emission Computed Tomography (PET-CT), Computed Tomography (CT) or magnetic resonance imaging (MRI).

One may make use of moderating materials between movable modular generators. For clinical systems there should be moderator material between the modular generators. Ideally the material can quickly position itself to the new location of the modular generators and also be a moderating material. As shown in FIG. 13D, liquid moderator 156 can be used to surround the modular generators 118, acting as a secondary moderator. The moderating material is shown between the movable modular generators. The liquid is contained in an appropriate liquid container. Liquids that also have good moderating properties can be used and are easily displaced by the modular generators when moving. For example, different grades of 3M™ Fluorinert™ Electronic Liquid (e.g. FC-40), which is non-conductive, thermally and chemically stable fluid, can be inserted between generators. Like Teflon it contains primarily fluorine atoms, making it an excellent moderator, and no hydrogen.

Stages of Moderation

Use of multiple modular generators in embodiments of the invention permits efficient use of modulator material, reducing size of moderator and shielding material and, thus, the reduction and size of the entire system. It also reduces the required flux density of fast neutrons by bringing the neutron sources closer to the patient and directing the limited number of neutrons to the cancer site in a more efficient fashion. The subject's body also becomes part of the equation of the moderating process. The fact that the neutrons are coming from multiple directions reduces local skin dose and localized body dose of healthy tissue. Rather than coming into the body at one location, the neutrons are coming from roughly 360 degrees around the body.

Moderation of fast neutrons in embodiments of the invention is a three-step process. In a first step (1) the pre-moderator 108 acts to reduce energy of the fast neutrons in as short a distance as practical with a minimal amount of gamma radiation produced in the process. The pre-moderator also serves as a medium to (2) transport high voltage and (3) cooling fluid to a fast neutron production titanium target 106. Combining these three functions ((1) moderation, (2) fluid transport and (3) high voltage transport) reduces distance and the amount of material between the fast neutron source and the patient, helping to maintain a maximum neutron flux finally delivered to the patient. Partially slowed neutrons can then pass into the secondary moderator 112 which continues the slowing process without undue production of gamma rays from, for example, hydrogen. In the case of small animal models, the selected moderator may be heavy water ($D_2O$). Neutron energy reduction is continued by the $D_2O$ without the generation of ~2.2 MeV gammas that would occur if materials composed of hydrogen were used.

For the case of irradiating tumors of depth greater than 3 cm in a human body, the neutrons need to be moderated to epithermal neutron energies. The human body also acts as a partial, final moderator. Thus, the epithermal energy neutrons are slowed further as they move through the body, and finally are slowed to thermal energies at the tumor site. Those skilled in the art will understand that the moderation is a statistical and random process that reduces the neutron energy with a variation or spread of the neutron energies. The process can also result in undesired gamma ray components (e.g. 2.2 MeV gammas from hydrogen capture of neutrons) which damage health cells. In embodiments of the invention, selection of the moderator material depends at least in part upon the desired energy of the neutrons at the body's skin to achieve maximum penetration to the cancer site while reducing (1) excess thermal energy components at the skin, (2) the cost and availability of the moderator material, and (3) harmful gamma ray components. Each generator's energy, yield, direction and moderation can be determined from moderation materials, the generator's voltage and acceleration current. Unlike in the prior art, dimensions of the moderator and content may be quickly changed. In some embodiments of the invention a liquid moderator (e.g. Fluorinert FC40) or a granular (e.g. $AlF_3$) moderator may be used. The modular generators are positioned in the liquid or granular moderator material, where they are free to move by mechanical means quickly between different cancer sites. In the prior art, the moderators and shields are large, massive and usually fixed relative to a single beam reactor or linear accelerator. The patient is usually moved relative to the fixed neutron source.

Using liquid or granular moderator materials permits a more efficient reduction of fast neutrons to epithermal energies while minimizing thermals and fast neutrons. Selection of the pre-moderator material is important for optimum neutron beam quality. Generally speaking, beam quality involves minimization of harmful components of radiation that accompany the production of thermal neutrons at the cancer site but also the minimization of the fast and thermal neutrons at the skin surface. In this process gamma rays are produced and, depending upon the cancer site, fast neutrons must be converted to the right energy so that they penetrate the body and deliver thermal neutrons to the tumor site with minimal irradiation of healthy tissue.

Moderating the neutrons to thermal energy can result in the skin being damaged. Indeed, the thermal neutron dose to the skin can be larger than the dose to the tumor. The body itself moderates and absorbs the neutrons as they penetrate the body. Selection of the moderator material requires materials that do not moderate the fast neutrons too quickly to thermal energies. Thermal neutrons can damage the skin, and if hydrogen atoms are present in the moderation process, then damaging gamma rays are also produced. Like the moderator, the human body also moderates and absorbs the neutrons. The desired required depth of penetration depends upon the location of the tumor in the body. Simulations show that penetration of thermal neutrons starting at the skin results in penetration depths of 3 to 5 cm before a large fraction of the neutrons are absorbed.

Teflon Moderator for Clinical Machine

When used as a Pre-moderator, Teflon (PTFE) can satisfy 6 of the 7 functions listed above. Indeed, on several of the attributes Teflon excels. For example, since Teflon does not have atomic hydrogen, gamma production is avoided, whereas the use of HDPE does have hydrogen and, therefore maximizes the thermal neutron moderation with and added 2.2 MeV gamma ray component. Selection of HDPE as the pre-moderator material results in production of thermal neutrons in a short distance from the Ti target, whereas the use of Teflon results in a slower rate of neutron energy reduction from 2.5 MeV permitting the production of epithermal neutrons for deeper penetration into the human body and no 2.2 MeV gammas.

Teflon can have a minimum high voltage in which surface arcs (flashovers or surface discharges) momentarily short out the high voltage, and lead to damage to the Teflon surface and possibly damage to the high voltage power supply. This is primarily a materials problem and not a structural problem (shape of the accelerator and Teflon shape and structure). Surface discharge along solid insulators in a vacuum in high voltage devices determines the maximum voltage between an anode and a cathode. The voltage hold-off capability of a solid insulator in vacuum is usually less than that of a vacuum gap of similar dimensions. O. Yamamoto et. al (Yamamoto, O; Takuma, T; Fukuda, M; Nagata, S; Sonoda, T "Improving withstand voltage by roughening the surface of an insulating spacer used in vacuum," IEEE TRANSACTIONS ON DIELECTRICS AND ELECTRICAL INSULATION (2003), 10(4): 550-556) has studied a simple and reliable method to improve surface insulation strength of a dielectric such as Teflon, PMMA, and $SiO_2$ by roughening the surface of the dielectric. Some experimental results have revealed that in a vacuum, charging along the surface of an insulating spacer precedes the flashover. The charging takes place through a process in which electrons are released from a triple junction where the cathode, insulator and vacuum meet, and propagate toward the anode, causing a secondary emission electron avalanche (SEEA) along the insulator surface. The dielectric (e.g. Teflon or HDPE) can hold charge like a battery or capacitor and then release it along the surface. This limits the use of plastics such as Teflon and HDPE as insulators and moderators inside the vacuum chamber of the neutron generator's acceleration chamber 100.

For short distances across Teflon (10 mm), Yamamoto found that roughing the surface (e.g. with sandpaper or sandblasting) affects the charging of various plastics (such as Teflon and HDPE), which decreases as roughness increases. Yamamoto used roughness up to 37.8 μm but had used lower voltage gradients and smaller dielectric thicknesses (10 mm). Studies in embodiments of the present invention find that larger surfaces (distances e.g. 8 inches) of Teflon can be roughened with roughness values of 5 microns and greater and achieve high voltages of 150-220 kV for distances greater than ~2 cm without flashover.

More importantly, the roughing method gives higher insulation strengths without time-consuming conditioning previously used. This provides a significant advantage and makes generators in embodiments of the present invention operational more quickly.

Depending on maximum field strength required, conditioning by the roughing process could take minutes or days. Below 1 MV $m^{-1}$, the conditioning process is relatively fast. Between 1 and 10 MV $m^{-1}$, the conditioning process takes longer. The best way to monitor how conditioning is going is to record the number of transient discharges (or sparks) per hour. At very high fields the arc rate might never get better than a few arcs per hour. A tolerable arc rate depends on the application. If no high voltage breakdown (arcs) can be tolerated, then the system must first be conditioned to a higher field, and then when the voltage is reduced to the operating level the arc rate drops almost to zero. For very high field strengths above 10 MV $m^{-1}$, it is very difficult to condition the electrodes to give an arc rate of zero. The electrode shape and material composition becomes very important at these field levels.

The Importance of the Human Body in the Moderation Process

The human body acts as a moderator to reduce the epithermal neutrons to thermal energies at the cancer site. The amount of neutron energy reduction by the human body depends at least in part upon the depth of the tumor in the body. This determines the maximum neutron flux for delivery to the patient. The desired reduction of the neutron's energy will depend upon the depth of the tumor in the human body. For example, with throat and neck cancers the reduction of the neutron energy to thermal energies is desired for maximum dose to the cancer site. For small animal models, thermal energies are also desired.

Dimension in the body from the skin (epidermis) to the cancer site can vary, requiring the neutron energy to be large enough for penetration to the cancer while still primarily at thermal energies, permitting capture by the boron and the destruction of cancer cells. For small animal models or skin cancer in humans, the neutrons can be at thermal energies. For cancers at deeper depths in the body, epithermal neutrons (0.025 to 0.4 eV) can be used. For deep tumors in the torso, such as, for example, pancreatic tumors, epithermal neutrons are required. Pancreatic tumors are deep in the torso and require epithermal neutrons at entrance to the body to penetrate to the tumor. Moderation of the epithermal neutrons occurs as they pass though the body. Simulations in various embodiments show that there are materials at the right thicknesses, such as Teflon, $^7$LiF and AlF$_3$, which produce the epithermal neutrons that penetrate the body and thermalize by the time they reach the depth of the tumor with a maximum neutron flux. In embodiments of the invention, this occurs while minimizing production of thermal neutrons at the skin.

Shape of a Clinical Machine to Match a Human Body

The shape of the patient's chamber in a machine may be contoured to fit the human body part to maximize radiation to the cancer site. The shape depends upon the body part to be irradiated and the location of the tumor. As shown in FIG. 13D, for glioblastoma 148 (brain cancer), modular generators 118 may be arranged in a close ring around the head 146 that maximizes neutron flux to the cancer site 148 in the brain. The intensity of each generator can be varied to achieve maximum thermal neutrons to the tumor while minimizing the dose to healthy tissue. As discussed above, applications in embodiments of this invention permit control of the distance of each generator from the cancer site. The cancer site may be mapped using radiographic means (CT scans) and/or MRIs. A treatment planning protocol can then be determined for the optimum use of the clinical neutron source. The intensity of the neutrons coming from each neutron generator can then be varied and the location of each individual generator can be optimized.

As shown in FIG. 13 D, an improvement of the moderator surrounding the modular generators is to suspend or surround the modular generators with a liquid 156 that does not contain hydrogen (a gamma producing source), but has modest atomic-number atoms like Fluorine, Carbon or Nitrogen. Various kinds of Fluorinert (tradename), FC-70 or FC-40, or FC3839 can be used. The fluid may be put between the modular generators and by mechanical means each modular generator can move independently of the other generators to a certain extent. This fluid can also absorb some heat from modular generators.

As shown in FIG. 13 D, an improvement of the moderator surrounding the modular generators is to suspend or surround the modular generators with a liquid 156 that does not contain hydrogen (a gamma producing source), but has modest atomic-number atoms like Fluorine, Carbon or Nitrogen. Various kinds of Fluorinert (tradename), FC-70 or FC-40, or FC3839 can be used. The fluid may be put between the modular generators and by mechanical means each modular generator can move independently of the other generators to a certain extent. This fluid can also absorb some heat from modular generators.

Generator Alignment

In embodiments of the present invention each stand-alone generator, as seen in FIG. 13D, for example, may be positioned and aligned to give a maximum flux and neutron distribution at the cancer site. Each generator is small enough in size and weight that the generators may be mechanically moved and positioned so that optimum neutron flux at the cancer site is achieved, depending upon the cancer's location and distribution. The generators may be arranged around a moderator whose radial thickness is optimized to deliver a maximum thermal neutron flux to the cancer site. Depending upon the body part being irradiated, the geometry can be circular or elliptical. By selecting the moderating material and radial thickness one can deliver thermal neutrons to the cancer site.

FIG. 14A shows an on-axis view of an exemplary clinical neutron source using multiple modular generators 118 for BNCT of a human head. This example uses eight modular generators 118 and assorted moderator materials coupled with reflecting and shielding material (e.g. graphite 144). Secondary moderators (166 and 170) can be composed of one or more materials. There are moderator spacing blocks 128 in one embodiment composed of the same material High Density Polyethylene (HDPE), Ultra High Molecular Weight polyethylene (UHMW), or (PTFE (Teflon)) as the secondary moderators. Blocks of these materials fit in between the modular generators and are adjacent to each generator's pre-moderator. They act as mechanical spacers as well as moderator components. The outside of this region, between and behind the modular generators 118, is filled with either graphite or lead 144 to serve as a neutron reflector and shield.

FIG. 14B also shows a side section view of the apparatus of FIG. 14A taken along a line through the top and bottom generators. There is additional moderator material in the front and behind the modular generators, extending a little above the pre-moderator. In our example, the cylindrical space 164 available for the patient's head is 52 cm deep and 30 cm in diameter. This space might be lined with 1-mm of cadmium 162 to shield against too large a thermal neutron dose to the patient's skin. Shield 162 is also shown in FIG. 14A. In other embodiments this space may be lined with $^6$LiF.

The exemplary arrangement as illustrated in FIGS. 14A and B has a secondary moderator consisting of multiple layers of 40% Al and 60% AlF$_3$ (166) and an additional moderating cylinder 170 of either $^7$LiF or D$_2$O. These materials are shown to be concentric rings in FIG. 14A. Since $^7$LiF or D$_2$O can be expensive, thicknesses were varied to obtain a desired neutron beam quality without over-using either $^7$LiF or D$_2$O. In the example shown in FIGS. 14A and 14 B the thickness ratio between the two segments is altered, the total moderator thickness is 34 cm, and the sources are R=52.5 cm from the origin (center of the brain). The effect of doing this varying these materials is plotted graphically in FIG. 15.

The reflector material graphite 144 is 30 cm thick in this example, the thickness of the Teflon 168, t, in front of the 2.5 MeV source is varied, and the portion 170 of the moderator is either $^7$LiF or D$_2$O. As t changes, the thickness of the Al/AlF$_3$ 166 of the moderator changes, with all other dimensions remaining constant. The target is embedded in the Teflon 168, UHMW or HDPE. Sources are titanium targets 106 being bombarded by deuterium ion beams 5.0 cm in diameter. Each target is emitting $4 \times 10^{10}$ neutron/sec. Eight modulator generators 118 emit $3.2 \times 10^{11}$ n/s total emission.

A concentration of $^{10}$B in the tumor and health tissue (e. g. skin) is known to be possible. $^{10}$B tumor concentration is assumed to be 50 ppm, while $^{10}$B in healthy tissue is 15 ppm. The relative biological effectiveness (RBE) for $^{10}$B in tumor is 2.7, and in healthy tissue is 1.3. Tumor and healthy tissue doses are calculated using the NRC and ICRP models for neutron RBE. The material $^7$LiF was the best performer and D$_2$O was second best.

An important main objective in these examples is to give a sufficient dose of neutrons to the cancer while minimizing the dose to the healthy tissue and not damaging it. FIG. 15 shows the performance for moderators with different values for tin cm and either $^7$LiF or D$_2$O in the secondary moderator. The ordinate R is the ratio of tumor dose at the origin to healthy tissue skin dose, and the tumor dose at the center of the brain assumed to be the site of the cancer. As can be seen from FIG. 15, $^7$LiF outperforms D$_2$O. The best performance is R=1.9 and a tumor dose in excess of 1.4 Sv/hr. A consequence of RBE is that a small percentage of fast neutrons is essential to obtain a high value for R; also, a reasonable number of epithermals is required to penetrate the target. Thus a combination of $^7$LiF and $D_2O$ may outperform either material alone.

A Need for Small Animal Neutron Sources

Development of boron delivery agents for BNCT is an ongoing and challenging task of high priority. A number of boron-10 containing delivery agents have been prepared for potential use in BNCT. With the development of new chemical synthetic techniques and increased knowledge of the biochemical requirements needed for an effective agent and their modes of delivery, a wide variety of new boron agents has emerged, but only two of these, oronophenylalanine (BPA) and sodium borocaptate (BSH) have been used clinically and have US FDA approval. Patient-derived xenograft (PDX) is created by transferring primary tumors from a patient into a mouse or small animal model. Tests of delivery and effectiveness of drugs to the cancer site can then be performed. In the prior art, only beamlines from nuclear reactors and linear accelerator structures can be used. A small laboratory neutron source, as in embodiments of this invention, is therefore valuable in the development and testing of new boron delivery drugs and their effectiveness in destroying the cancer site.

As compared to a clinical delivery system, a smaller number of stand-alone generators such as generators 118 is needed for a delivery system for a small animal such as a mouse. The modular generators used have a slab wall angle of α=0 (see α defined in FIG. 12 A). The secondary moderator may be a separate container of heavy water ($D_2O$).

Since the small animal target is indeed small, the secondary moderator volume can be reduced, and the compact modular generators can be moved close to it permitting the modular generators to be closer to the animal target. Thus, the neutron flux at the cancer site is increased, and with proper selection of moderator material and size, will still be able to moderate the neutrons to IAEA standards. In addition, by moving closer, the number of generators can be reduced while still maintaining a high thermal neutron flux at the cancer site.

In our example of the new art for a small animal source, we can use four modular generators 118 to emit enough thermal neutrons at the cancer site. We can use the modular generators of 12 A, B, C with the slab wall angle of α=0. This makes the pre-moderator 108 a rectangular cuboid (or "rectangular slab" of). FIG. 16A is a perspective view of a modular generator having such a rectangular pre-moderator 108, making it suitable for arrangements of four generators in a rectangular array, as shown in FIG. 16B. In FIG. 16B the four modular generators are arranged around a secondary moderator 112, which in one embodiment may be a container of heavy water or granulated moderator material. FIG. 16C is a cross section view of the arrangement of FIG. 16B, taken along section line4 16C-16C of FIG. 16B. The elements previously annotated for modular generators are reused in FIGS. 16 A, B and C.

FIG. 16D is an exploded view where the four generators 118 are moved back from the small heavy water moderator 112. Each generator 118 has a pre-moderator 108 with a fast neutron generator with a titanium target 106. A deuterium ion beam is generated by a plasma ion source 102 and accelerated in an acceleration chamber 100 to the titanium target 106, where the DD fusion reaction occurs releasing fast 2.5 MeV neutrons. This description is all common to the descriptions or other embodiments in the specification. The neutrons generated pass through a pre-moderator 108, where they are partially moderated to thermal neutron energies. They then pass into the moderator block 112 where they are further moderated, reducing the energy of fast neutrons to thermal neutron energies. The thermal neutrons then enter a cylindrical mouse chamber 114 where they enter the small animal 116.

The pre-moderator is designed to slow the fast neutrons to thermal neutrons by scattering the fast neutrons via collisions with the hydrogen in the HDPE or UHMW plastics. The distance the 2.5 MeV neutrons have to traverse is approximately 3 to 5 cm, wherein approximately 50% of the neutrons lose enough of their energy to be classified as thermal neutrons. These neutrons, containing both thermal and fast neutron components, can then travel into the moderator box 112, where they are further moderated by collisions with deuterium atoms. Roughly speaking, the HDPE with its hydrogen-atoms moderates the neutrons to thermal energies over a short distance; the thermalized neutrons then penetrate the cylindrical chamber 114 wherein they place the small animal 116. The small animal model is used to test the delivery of boron to the cancer site.

For the pre-moderator, high density polyethylene (HDPE) is optimum for producing the maximum flux of thermal neutrons. As in the case of the clinical generator, it is desired to produce a maximum thermal flux at the cancer site. A mouse is a small object, and penetration of thermal neutrons to the cancer site can easily be achieved. Moderation of the fast neutrons to thermal energies is desired with minimum production of gamma radiation, which is harmful to the healthy cells. As those skilled in the art will understand, hydrogen atoms are excellent at scattering fast neutrons, resulting in moderation of the neutrons to thermal energies in the shortest path length in the moderating material. Indeed, using 5-6 cm of high-density polyethylene (HDPE) or UHMW plastic results in moderation of about 50% of 2.5 MeV neutrons to thermal energies. Further moderation of the neutrons by longer distances in the HDPE results in more fast neutrons being converted to thermal energies. However, this results in reduction of the total flux ($n/cm^2$) that is available since the neutrons are being emitted in a 4π solid angle. Hydrogen capture of neutrons produces high energy gamma radiation, which is destructive to both healthy and cancerous cells. Adding another moderator to further thermalize the neutrons is accomplished by the use of heavy water ($D_2O$).

The skilled person will understand that the embodiments described in this application are exemplary, and not limiting. Many variations may well fall within the scope of the invention, which is limited only by the scope of the following claims.

What is claimed is:

1. A Boron neutron cancer treatment system, comprising: a secondary moderator having a central treatment chamber for a subject; and eight identical neutron generators, each comprising a pre-moderator block of moderating material having an upper surface, a lower surface, a first and a second end, opposite side surfaces angled inward by forty-five degrees along at least a portion of the height, a first length, a first width less than the first length, and a first thickness, a cylindrical acceleration chamber having a first diameter the first width of the pre-moderator block, sealed at one end to the upper surface of the pre-moderator block adjacent the first end of the pre-moderator block, with a vertical axis perpendicular to the upper surface, the acceleration chamber having a height and a top cover at a second end away from the pre-moderator block, a vacuum pump engaging the acceleration chamber at a right angle to the vertical axis, evacuating the acceleration chamber to a high vacuum, a plasma ion chamber opening into the acceleration chamber through an ion extraction iris through the top cover of the acceleration chamber on the vertical axis of the acceleration chamber, a gas source providing deuterium gas to the plasma ion chamber, a microwave energy source ionizing the gas in the plasma ion chamber, a cylindrical primary isolation well extending a distance into the pre-moderator block from the upper surface, centered on the vertical axis of the acceleration chamber, a secondary isolation well in a shape of a hollow cylinder surrounding the primary isolation well, to a depth somewhat less than the distance of the primary isolation well, within the first diameter of the acceleration chamber, a water-cooled titanium target disk having a target surface orthogonal to the axis of the acceleration chamber, the target disk having a diameter smaller then a diameter of the isolation well, positioned at a lower extremity of the isolation well, the target disk biased to a negative DC voltage, and electrically grounded metal cladding covering all otherwise exposed surfaces of the pre-moderator block;

wherein the eight neutron generators are positioned around the secondary moderator with the axis of each acceleration chamber passing through the center of the treatment chamber, and with the angled sides of the neutron generators fully adjacent.

2. The system of claim 1 further comprising eight rectangular spacing blocks of moderator material, one spacing block placed between each adjacent neutron generator with sides of the spacing blocks fully adjacent with the angled sides of the neutron generators.

3. The system of claim 1 wherein the secondary moderator is shaped to fill all volume between the neutron generators and the central treatment chamber.

4. The system of claim 1 wherein the secondary moderator is a block or blocks of solid moderator material.

5. The system of claim 1 wherein the secondary moderator is a container filled with heavy water.

6. The system of claim 1 wherein the secondary moderator is a container filled with granulated moderator material.

\* \* \* \* \*